(12) United States Patent
Harrison et al.

(10) Patent No.: US 12,178,726 B2
(45) Date of Patent: Dec. 31, 2024

(54) NON-FORESHORTENING STENT

(71) Applicant: Vesper Medical, Inc., Malvern, PA (US)

(72) Inventors: William James Harrison, Signal Mtn, TN (US); Michael A Longo, Glenmoore, PA (US)

(73) Assignee: VESPER MEDICAL, INC., Wayne, PA (US)

( * ) Notice: Subject to any disclaimer, the term of this patent is extended or adjusted under 35 U.S.C. 154(b) by 641 days.

(21) Appl. No.: 17/064,770

(22) Filed: Oct. 7, 2020

(65) Prior Publication Data

US 2021/0052405 A1 Feb. 25, 2021

Related U.S. Application Data

(63) Continuation of application No. 15/684,626, filed on Aug. 23, 2017, now Pat. No. 10,849,769.

(51) Int. Cl.
*A61F 2/95* (2013.01)
*A61F 2/915* (2013.01)

(52) U.S. Cl.
CPC ............ *A61F 2/915* (2013.01); *A61F 2/9522* (2020.05); *A61F 2002/91541* (2013.01);
(Continued)

(58) Field of Classification Search
CPC .... A61F 2/86; A61F 2/89; A61F 2/915; A61F 2002/91508; A61F 2002/91516;
(Continued)

(56) References Cited

U.S. PATENT DOCUMENTS

| 5,449,373 | A | 9/1995 | Pinchasik et al. |
| 5,807,404 | A | 9/1998 | Richter |
| 5,827,321 | A | 10/1998 | Roubin et al. |
| 5,836,966 | A | 11/1998 | St. Germain |

(Continued)

FOREIGN PATENT DOCUMENTS

| CN | 103476365 A | 12/2013 |
| EP | 1260197 | 11/2002 |

(Continued)

OTHER PUBLICATIONS

Office Action, dated Apr. 12, 2022, received in connection with corresponding JP Patent Application No. 2020-511159 (and English translation).

(Continued)

*Primary Examiner* — Dianne Dornbusch

(57) ABSTRACT

Self-expending stents that include circumferential rings of alternating interconnected struts connected by flexible connectors. The struts of the rings and flexible connectors have a structure, including areas of expanded or reduced width or thickness, to account for venous applications. When used for venous applications, the stents convey benefit from configurations that improve flexibility (due to the greater elasticity of venous applications) while maintaining enough stiffness to resist pressure on the venous structure in selected areas (such as for the May-Thurner syndrome). The stents include particular structural characteristics—often expressed as ratios between different measurements—that are particularly advantageous for (although not limited to) venous applications.

20 Claims, 9 Drawing Sheets

(52) U.S. Cl.
CPC ............. *A61F 2002/91558* (2013.01); *A61F 2002/91575* (2013.01); *A61F 2002/91583* (2013.01)

(58) Field of Classification Search
CPC .... A61F 2002/91525; A61F 2002/9155; A61F 2002/91558; A61F 2002/91566; A61F 2002/91575; A61F 2002/91583; A61F 2250/0036; A61F 2250/0039
See application file for complete search history.

(56) References Cited

U.S. PATENT DOCUMENTS

| | | | |
|---|---|---|---|
| 5,843,120 A | 12/1998 | Israel et al. | |
| 5,843,175 A * | 12/1998 | Frantzen | A61F 2/915 623/1.15 |
| 5,868,780 A | 2/1999 | Lashinski et al. | |
| 5,868,782 A | 2/1999 | Frantzen | |
| 5,911,754 A | 6/1999 | Kanesaka et al. | |
| 5,922,005 A | 7/1999 | Richter et al. | |
| 5,938,697 A | 8/1999 | Killion et al. | |
| 5,964,798 A | 10/1999 | Imran | |
| 5,972,018 A | 10/1999 | Israel et al. | |
| 6,027,526 A | 2/2000 | Limon et al. | |
| 6,033,433 A | 3/2000 | Her et al. | |
| 6,042,606 A | 3/2000 | Frantzen | |
| 6,059,811 A | 5/2000 | Pinchasik et al. | |
| 6,068,656 A | 5/2000 | Von Oepen | |
| 6,083,259 A | 7/2000 | Frantzen | |
| 6,106,548 A | 8/2000 | Roubin et al. | |
| 6,113,627 A | 9/2000 | Jang | |
| 6,123,721 A | 9/2000 | Jang | |
| 6,146,403 A | 11/2000 | St. Germain | |
| 6,156,052 A | 12/2000 | Richter | |
| 6,179,868 B1 | 1/2001 | Burpee et al. | |
| 6,183,507 B1 | 2/2001 | Lashinski et al. | |
| 6,190,403 B1 | 2/2001 | Fischell et al. | |
| 6,200,334 B1 | 3/2001 | Jang | |
| 6,203,569 B1 | 3/2001 | Wijay | |
| 6,235,053 B1 | 5/2001 | Jang | |
| 6,241,762 B1 | 6/2001 | Shanley | |
| 6,261,318 B1 | 7/2001 | Lee et al. | |
| 6,261,319 B1 | 7/2001 | Kveen et al. | |
| 6,287,336 B1 | 9/2001 | Globerman et al. | |
| 6,299,635 B1 | 10/2001 | Frantzen | |
| 6,309,414 B1 | 10/2001 | Rolando et al. | |
| 6,325,821 B1 | 12/2001 | Gaschino et al. | |
| 6,325,825 B1 | 12/2001 | Kula et al. | |
| 6,402,777 B1 | 6/2002 | Globerman et al. | |
| 6,416,543 B1 * | 7/2002 | Hilaire | A61F 2/91 623/1.15 |
| 6,428,570 B1 | 8/2002 | Globerman | |
| 6,443,982 B1 | 9/2002 | Israel et al. | |
| 6,451,049 B2 | 9/2002 | Vallana et al. | |
| 6,461,380 B1 | 10/2002 | Cox | |
| 6,461,381 B2 | 10/2002 | Israel et al. | |
| 6,464,722 B2 | 10/2002 | Israel et al. | |
| 6,475,236 B1 | 11/2002 | Roubin | |
| 6,478,816 B2 | 11/2002 | Kveen et al. | |
| 6,485,508 B1 | 11/2002 | McGuinness | |
| 6,485,509 B2 | 12/2002 | Killion et al. | |
| 6,497,723 B1 | 12/2002 | Starck et al. | |
| 6,540,774 B1 | 4/2003 | Cox | |
| 6,540,775 B1 * | 4/2003 | Fischell | A61F 2/91 623/1.15 |
| 6,602,282 B1 | 8/2003 | Yan | |
| 6,605,110 B2 | 8/2003 | Harrison | |
| 6,635,084 B2 | 10/2003 | Israel et al. | |
| 6,638,300 B1 | 10/2003 | Frantzen | |
| 6,641,609 B2 | 11/2003 | Globerman | |
| 6,660,019 B1 | 12/2003 | Richter et al. | |
| 6,679,911 B2 | 1/2004 | Burgermeister | |
| 6,682,554 B2 | 1/2004 | Oepen et al. | |
| 6,692,522 B1 | 2/2004 | Richter | |
| 6,699,281 B2 | 3/2004 | Vallana et al. | |
| 6,706,061 B1 | 3/2004 | Fischell et al. | |
| 6,709,453 B2 | 3/2004 | Pinchasik et al. | |
| 6,730,116 B1 | 5/2004 | Wolinsky et al. | |
| 6,746,479 B2 | 6/2004 | Her et al. | |
| 6,761,731 B2 | 7/2004 | Majercak | |
| 6,764,506 B2 | 7/2004 | Roubin et al. | |
| 6,786,922 B2 | 9/2004 | Schaeffer | |
| 6,790,227 B2 | 9/2004 | Burgermeister | |
| 6,818,015 B2 | 11/2004 | Hankh et al. | |
| 6,923,829 B2 | 8/2005 | Boyle et al. | |
| 6,939,373 B2 | 9/2005 | Gomez et al. | |
| 6,945,993 B2 | 9/2005 | Kveen et al. | |
| 7,004,968 B2 | 2/2006 | Lootz et al. | |
| D516,723 S | 3/2006 | Shanley | |
| 7,029,493 B2 | 4/2006 | Majercak et al. | |
| 7,037,330 B1 | 5/2006 | Rivelli, Jr. et al. | |
| 7,060,088 B1 | 6/2006 | Fischell et al. | |
| 7,060,090 B2 | 6/2006 | Thornton | |
| 7,070,614 B1 | 7/2006 | Neuss et al. | |
| 7,131,993 B2 | 11/2006 | Gregorich | |
| 7,135,038 B1 | 11/2006 | Limon | |
| 7,141,062 B1 | 11/2006 | Pinchasik et al. | |
| 7,147,661 B2 | 12/2006 | Chobotov et al. | |
| 7,247,166 B2 | 7/2007 | Pienknagura | |
| 7,273,494 B2 | 9/2007 | Rolando et al. | |
| 7,316,710 B1 | 1/2008 | Cheng et al. | |
| 7,326,243 B2 | 2/2008 | Kveen et al. | |
| 7,344,563 B2 | 3/2008 | Vallana et al. | |
| 7,357,813 B2 | 4/2008 | Burgermeister | |
| 7,402,169 B2 | 7/2008 | Killion | |
| 7,465,315 B2 | 12/2008 | Morris et al. | |
| 7,485,130 B2 | 2/2009 | St. Germain | |
| 7,527,644 B2 | 5/2009 | Mangiardi et al. | |
| 7,611,531 B2 * | 11/2009 | Calisse | A61F 2/915 623/1.15 |
| 7,621,947 B2 | 11/2009 | Richter et al. | |
| 7,648,526 B2 | 1/2010 | Sano et al. | |
| 7,686,843 B2 | 3/2010 | Moore | |
| 7,731,746 B2 | 6/2010 | Kveen et al. | |
| 7,766,960 B2 | 8/2010 | Alexander et al. | |
| 7,806,918 B2 | 10/2010 | Nissl et al. | |
| 7,862,607 B2 | 1/2011 | McDermott et al. | |
| 7,896,912 B2 | 3/2011 | Shanley | |
| 8,012,196 B2 | 9/2011 | Smith et al. | |
| 8,016,874 B2 | 9/2011 | Casey | |
| 8,052,734 B2 | 11/2011 | Shanley | |
| 8,128,679 B2 | 3/2012 | Casey | |
| 8,206,427 B1 | 6/2012 | Ryan et al. | |
| 8,211,163 B2 | 7/2012 | Dakin et al. | |
| 8,221,489 B2 | 7/2012 | Issenmann et al. | |
| 8,257,424 B2 * | 9/2012 | Orlowski | A61F 2/915 623/1.15 |
| 8,267,991 B2 | 9/2012 | De Scheerder et al. | |
| 8,317,854 B1 | 11/2012 | Ryan et al. | |
| 8,317,859 B2 | 11/2012 | Snow et al. | |
| 8,337,544 B2 | 12/2012 | Osman et al. | |
| 8,348,990 B2 | 1/2013 | Boyle et al. | |
| 8,470,021 B2 | 6/2013 | Magnuson et al. | |
| 8,524,132 B2 | 9/2013 | Von Oepen et al. | |
| 8,562,665 B2 | 10/2013 | Jang | |
| 8,647,379 B2 | 2/2014 | McDermott et al. | |
| 8,652,196 B2 | 2/2014 | Nissl | |
| 8,668,731 B2 | 3/2014 | Kveen et al. | |
| 8,888,837 B2 | 11/2014 | Obradović et al. | |
| 8,974,514 B2 | 3/2015 | Anukhin et al. | |
| 9,066,825 B2 | 6/2015 | Chanduszko | |
| 9,168,161 B2 * | 10/2015 | Donovan | A61F 2/88 |
| 9,320,627 B2 | 4/2016 | Casey | |
| 9,375,810 B2 | 6/2016 | Mangiardi | |
| 9,381,103 B2 | 7/2016 | Abunassar | |
| 9,408,727 B2 | 8/2016 | Ainsworth et al. | |
| 9,498,360 B2 | 11/2016 | Layman et al. | |
| 9,554,927 B2 | 1/2017 | Bales, Jr. et al. | |
| 9,561,123 B2 | 2/2017 | Bales, Jr. et al. | |
| 9,622,850 B2 | 4/2017 | Bebb | |
| 9,649,211 B2 | 5/2017 | Bonsignore et al. | |
| 9,655,998 B2 | 5/2017 | Gemborys | |
| 9,668,895 B2 | 6/2017 | Dreher | |

(56) References Cited

U.S. PATENT DOCUMENTS

| | | |
|---|---|---|
| 9,668,898 B2 | 6/2017 | Wong |
| 9,693,860 B2 | 7/2017 | Sandstrom et al. |
| 9,700,448 B2 | 7/2017 | Snow et al. |
| 9,707,110 B2 | 7/2017 | McDermott et al. |
| 9,724,220 B2 | 8/2017 | Rasmussen |
| 9,763,818 B2 | 9/2017 | Trollsas et al. |
| 9,770,348 B2 | 9/2017 | Wack |
| 9,795,496 B2 | 10/2017 | Armstrong et al. |
| 9,839,538 B2 | 12/2017 | Grewe et al. |
| 9,839,540 B2 | 12/2017 | Armstrong et al. |
| 9,855,159 B2 | 1/2018 | Baba |
| 9,907,685 B2 | 3/2018 | Trollsas et al. |
| 9,937,280 B2 | 4/2018 | Yan et al. |
| 2001/0010014 A1 | 7/2001 | Trozera |
| 2001/0014822 A1 | 8/2001 | Milo |
| 2001/0047200 A1 | 11/2001 | White et al. |
| 2002/0013616 A1 | 1/2002 | Carter et al. |
| 2002/0042647 A1 | 4/2002 | Jang |
| 2002/0042648 A1 | 4/2002 | Schaldach et al. |
| 2002/0045934 A1 | 4/2002 | Jang |
| 2002/0058990 A1 | 5/2002 | Jang |
| 2002/0072793 A1 | 6/2002 | Rolando et al. |
| 2002/0107563 A1 | 8/2002 | Shanley |
| 2003/0009214 A1 | 1/2003 | Shanley |
| 2003/0014102 A1 | 1/2003 | Hong et al. |
| 2003/0068355 A1 | 4/2003 | Shanley |
| 2003/0088310 A1 | 5/2003 | Hansen et al. |
| 2003/0100941 A1 | 5/2003 | Fischell et al. |
| 2003/0105513 A1 | 6/2003 | Moriuchi et al. |
| 2003/0105517 A1 | 6/2003 | White et al. |
| 2004/0006382 A1 | 1/2004 | Sohier |
| 2004/0054398 A1 | 3/2004 | Cully et al. |
| 2004/0054400 A1 | 3/2004 | Granada |
| 2004/0102833 A1 | 5/2004 | Girton et al. |
| 2004/0102835 A1 | 5/2004 | Israel et al. |
| 2004/0133265 A1 | 7/2004 | Duffy |
| 2004/0143321 A1 | 7/2004 | Litvack et al. |
| 2004/0249445 A1 | 12/2004 | Rosenthal et al. |
| 2004/0254627 A1 | 12/2004 | Thompson et al. |
| 2004/0267350 A1 | 12/2004 | Roubin et al. |
| 2005/0004657 A1 | 1/2005 | Burgermeister |
| 2005/0021130 A1 | 1/2005 | Kveen et al. |
| 2005/0060024 A1 | 3/2005 | Lee et al. |
| 2005/0080479 A1 | 4/2005 | Feng et al. |
| 2005/0107865 A1 | 5/2005 | Clifford et al. |
| 2005/0182479 A1* | 8/2005 | Bonsignore ............ A61F 2/915 623/1.15 |
| 2005/0278016 A1 | 12/2005 | Welsh et al. |
| 2005/0288769 A1 | 12/2005 | Globerman |
| 2006/0004435 A1 | 1/2006 | Burgermeister et al. |
| 2006/0025852 A1 | 2/2006 | Armstrong et al. |
| 2006/0100692 A1* | 5/2006 | Burgermeister ...... A61L 27/045 623/1.18 |
| 2006/0122688 A1 | 6/2006 | Shanley et al. |
| 2006/0129227 A1 | 6/2006 | Hengelmolen |
| 2006/0173531 A1 | 6/2006 | Richter |
| 2006/0224233 A1 | 10/2006 | Grinfeld et al. |
| 2006/0235506 A1 | 10/2006 | Ta et al. |
| 2006/0287707 A1 | 12/2006 | Roeder et al. |
| 2007/0010869 A1 | 1/2007 | Sano |
| 2007/0135901 A1 | 6/2007 | Burgermeister et al. |
| 2007/0168010 A1 | 7/2007 | Goshgarian |
| 2007/0213806 A1 | 9/2007 | Roubin et al. |
| 2007/0213807 A1 | 9/2007 | Roubin et al. |
| 2007/0219613 A1 | 9/2007 | Kao et al. |
| 2007/0288084 A1 | 12/2007 | Lee et al. |
| 2008/0009938 A1 | 1/2008 | Huang et al. |
| 2008/0051878 A1 | 2/2008 | Cheng et al. |
| 2008/0097579 A1 | 4/2008 | Shanley et al. |
| 2008/0140181 A1 | 6/2008 | Reynolds et al. |
| 2008/0288048 A1 | 11/2008 | Rolando et al. |
| 2009/0005858 A1 | 1/2009 | Young et al. |
| 2009/0012599 A1 | 1/2009 | Broome et al. |
| 2009/0018641 A1 | 1/2009 | Binkert |
| 2009/0062899 A1 | 3/2009 | Dang et al. |
| 2009/0105809 A1* | 4/2009 | Lee ........................ A61F 2/91 623/1.33 |
| 2009/0163989 A1 | 6/2009 | Contiliano et al. |
| 2010/0004728 A1 | 1/2010 | Rao et al. |
| 2010/0004736 A1 | 1/2010 | Rolando et al. |
| 2010/0057190 A1 | 3/2010 | Issenmann |
| 2010/0131044 A1 | 5/2010 | Patel |
| 2010/0191324 A1 | 7/2010 | Klocke |
| 2010/0222864 A1 | 9/2010 | Rivelli, Jr. et al. |
| 2010/0241216 A1 | 9/2010 | Rolando et al. |
| 2010/0292777 A1 | 11/2010 | Meyer et al. |
| 2011/0125251 A1 | 2/2011 | Cottone et al. |
| 2011/0071616 A1 | 3/2011 | Clarke et al. |
| 2011/0106237 A1 | 5/2011 | Bonsignore et al. |
| 2011/0112626 A1 | 5/2011 | Van Der Leest |
| 2011/0137407 A1 | 6/2011 | Nguyen et al. |
| 2011/0190871 A1 | 8/2011 | Trollsas et al. |
| 2011/0230957 A1 | 9/2011 | Bonsignore et al. |
| 2011/0251673 A1 | 10/2011 | Ehrlinspiel et al. |
| 2012/0043703 A1 | 2/2012 | Von Oepen et al. |
| 2012/0046729 A1 | 2/2012 | Von Oepen et al. |
| 2012/0046730 A1 | 2/2012 | Von Oepen et al. |
| 2012/0046731 A1 | 2/2012 | Von Oepen et al. |
| 2012/0046733 A1 | 2/2012 | Von Oepen et al. |
| 2012/0046739 A1 | 2/2012 | Von Oepen et al. |
| 2012/0073733 A1 | 3/2012 | Ngo et al. |
| 2012/0143312 A1 | 6/2012 | Brown |
| 2012/0158116 A1 | 6/2012 | Fischell et al. |
| 2012/0165920 A1 | 6/2012 | Meyer et al. |
| 2012/0172972 A1 | 7/2012 | Meyer et al. |
| 2012/0197384 A1 | 8/2012 | Lee et al. |
| 2012/0277844 A1 | 11/2012 | Wu |
| 2012/0310327 A1 | 12/2012 | McHugo |
| 2013/0144375 A1 | 6/2013 | Giasolli et al. |
| 2013/0178928 A1 | 7/2013 | Vyas et al. |
| 2013/0236498 A1 | 9/2013 | Mangiardi |
| 2013/0304192 A1 | 11/2013 | Chanduszko |
| 2013/0325141 A1 | 12/2013 | Gill et al. |
| 2014/0200647 A1 | 7/2014 | Abunassar |
| 2014/0277365 A1 | 9/2014 | Gillespie |
| 2014/0277378 A1 | 9/2014 | Lane et al. |
| 2015/0105852 A1 | 4/2015 | Noffke et al. |
| 2015/0209167 A1 | 7/2015 | Mangiardi |
| 2015/0250580 A1 | 9/2015 | Besselink |
| 2016/0184079 A1 | 6/2016 | Scutti et al. |
| 2016/0235562 A1 | 8/2016 | Casey |
| 2016/0250052 A1 | 9/2016 | Kaspar |
| 2016/0262915 A1 | 9/2016 | Mangiardi |
| 2016/0287418 A1 | 10/2016 | Cheng et al. |
| 2016/0367388 A1 | 12/2016 | Skousen et al. |
| 2017/0035548 A1 | 2/2017 | Bebb et al. |
| 2017/0071768 A1 | 3/2017 | Krieger et al. |
| 2017/0086994 A1 | 3/2017 | Bales et al. |
| 2017/0100267 A1 | 4/2017 | Bales et al. |
| 2017/0224878 A1 | 8/2017 | Gemborys |
| 2017/0265998 A1 | 9/2017 | Sandstrom et al. |
| 2017/0312104 A1 | 11/2017 | McDermott et al. |
| 2017/0312105 A1 | 11/2017 | McDermott et al. |
| 2017/0340464 A1 | 11/2017 | Kovach et al. |

FOREIGN PATENT DOCUMENTS

| | | |
|---|---|---|
| EP | 1374800 | 4/2012 |
| EP | 2967828 | 1/2016 |
| JP | 2002530146 A | 9/2002 |
| WO | 2000030563 A1 | 6/2000 |
| WO | 2003049642 | 6/2003 |
| WO | 2005110284 | 11/2005 |
| WO | 2008008291 | 1/2008 |
| WO | 2014144683 | 9/2014 |
| WO | 2015038790 | 3/2015 |

OTHER PUBLICATIONS

Office Action and Search Report, dated Aug. 3, 2022, received in connection with corresponding CN Patent Application No. 201880054742.9 (and English translation).

(56) References Cited

OTHER PUBLICATIONS

International Search Report and Written Opinion dated Nov. 19, 2018, from International Application No. PCT/US2018/047639, 15 pages.

\* cited by examiner

NON-FORESHORTENING STENT

CROSS REFERENCE TO RELATED APPLICATIONS

This application is a continuation of U.S. patent application Ser. No. 15/684,626, filed Aug. 23, 2017, granted as U.S. Pat. No. 10,849,769 on Dec. 1, 2020, which is hereby incorporated by reference in its entirety, for all purposes as if fully set forth herein

BACKGROUND

Field of the Invention

Disclosed herein are stents for implantation within the body and methods for delivery and/or deployment. Certain embodiments disclosed herein may be used in procedures to treat May-Thurner syndrome and/or deep venous thrombosis and the resulting post-thrombotic syndrome.

Description of the Related Art

May-Thurner syndrome, also known as iliac vein compression syndrome, is a condition in which compression of the common venous outflow tract of the left lower extremity may cause various adverse effects, including, but not limited to, discomfort, swelling, pain, and/or deep venous thrombosis (DVT) (commonly known as blood clots). May-Thurner syndrome occurs when the left common iliac vein is compressed by the overlying right common iliac artery, leading to stasis of blood, which may cause the formation of blood clots in some individuals. Other, less common, variations of May-Thurner syndrome have been described, such as compression of the right common iliac vein by the right common iliac artery.

While May-Thurner syndrome is thought to represent between two to five percent of lower-extremity venous disorders, it frequently goes unrecognized. Nevertheless, it is generally accepted that May-Thurner syndrome is about three times more common in women than it is in men and typically manifests itself between the age of twenty and forty. Patients exhibiting both hypercoagulability and left lower extremity thrombosis may be suffering from May-Thurner syndrome. To confirm that diagnosis, it may be necessary to rule out other causes for hypercoagulable state, for example by evaluating levels of antithrombin, protein C, protein S, factor V Leiden, and prothrombin G20210A.

By contrast to the right common iliac vein, which ascends almost vertically parallel to the inferior vena cava, the left common iliac vein takes a more transverse course. Along this course, it lies under the right common iliac artery, which may compress it against the lumbar spine. Iliac vein compression is a frequent anatomic variant—it is thought that as much as 50% luminal compression of the left iliac vein occurs in a quarter of healthy individuals. However, compression of the left common iliac vein becomes clinically significant only if such compression causes appreciable hemodynamic changes in venous flow or venous pressure, or if it leads to acute or chronic deep venous thrombosis, which will be discussed in more detail below. In addition to the other problems associated with compression, the vein may also develop intraluminal fibrous spurs from the effects of the chronic pulsatile compressive force from the overlying artery.

The narrowed, turbulent channel associated with May-Thurner syndrome may predispose the afflicted patient to thrombosis. And, the compromised blood flow often causes collateral blood vessels to form—most often horizontal transpelvis collaterals, connecting both internal iliac veins to create additional outflow possibilities through the right common iliac vein. Sometimes vertical collaterals are formed, most often paralumbar, which can cause neurological symptoms, like tingling and numbness.

Current best practices for the treatment and/or management of May-Thurner syndrome is proportional to the severity of the clinical presentation. Leg swelling and pain is best evaluated by vascular specialists, such as vascular surgeons, interventional cardiologists, and interventional radiologists, who both diagnose and treat arterial and venous diseases to ensure that the cause of the extremity pain is evaluated. Diagnosis of May-Thurner syndrome is generally confirmed one or more imaging modalities that may include magnetic resonance venography, and venogram, which, because the collapsed/flattened left common iliac may not be visible or noticed using conventional venography, are usually confirmed with intravascular ultrasound, To prevent prolonged swelling or pain as downstream consequences of the left common iliac hemostasis, blood flow out of the leg should be improved/increased. Early-stage or uncomplicated cases may be managed simply with compression stockings. Late-stage or severe May-Thurner syndrome may require thrombolysis if there is a recent onset of thrombosis, followed by, angioplasty and stenting of the iliac vein after confirming the diagnosis with a venogram or an intravascular ultrasound. A stent may be used to support the area from further compression following angioplasty. However, currently available stenting options suffer from several complications—including severe foreshortening, lack of flexibility (which can force the vessel to straighten excessively), vessel wear and eventual perforation, increased load on and deformation of the stent causing early fatigue failure, and/or impedence of flow in the overlying left iliac artery potentially causing peripheral arterial disease. The compressed, narrowed outflow channel present in May-Thurner syndrome may cause stasis of the blood, which an important contributing factor to deep vein thrombosis.

Some patients suffering from May-Thurner syndrome may exhibit thrombosis while others may not. Nevertheless, those patients that do not experience thrombotic symptoms may still experience thrombosis at any time. If a patient has extensive thrombosis, pharmacologic and/or mechanical (i.e., pharmacomechanical) thrombectomy may be necessary. The hemostasis caused by May-Thurner syndrome has been positively linked to an increased incidence of deep vein thrombosis ("DVT").

Deep vein thrombosis, or deep venous thrombosis, is the formation of a blood clot (thrombus) within a deep vein, predominantly in the legs. The right and left common iliac are common locations for deep vein thrombosis, but other locations of occurrence are common. Non-specific symptoms associated with the condition may include pain, swelling, redness, warmness, and engorged superficial veins. Pulmonary embolism, a potentially life-threatening complication of deep vein thrombosis, is caused by the detachment of a partial or complete thrombus that travels to the lungs. Post-thrombotic syndrome, another long-term complication associated with deep venous thrombosis, is a medical condition caused by a reduction in the return of venous blood to the heart and can include the symptoms of chronic leg pain, swelling, redness, and ulcers or sores.

Deep vein thrombosis formation typically begins inside the valves of the calf veins, where the blood is relatively oxygen deprived, which activates certain biochemical pathways. Several medical conditions increase the risk for deep vein thrombosis, including cancer, trauma, and antiphospholipid syndrome. Other risk factors include older age, surgery, immobilization (e.g., as experienced with bed rest, orthopedic casts, and sitting on long flights), combined oral contraceptives, pregnancy, the postnatal period, and genetic factors. Those genetic factors include deficiencies with antithrombin, protein C, and protein S, the mutation of Factor V Leiden, and the property of having a non-O blood type. The rate of new cases of deep vein thrombosis increases dramatically from childhood to old age; in adulthood, about 1 in 1000 adults develops the condition annually.

Common symptoms of deep vein thrombosis include pain or tenderness, swelling, warmth, redness or discoloration, and distention of surface veins, although about half of those with the condition have no symptoms. Signs and symptoms alone are not sufficiently sensitive or specific to make a diagnosis, but when considered in conjunction with known risk factors can help determine the likelihood of deep vein thrombosis. Deep vein thrombosis is frequently ruled out as a diagnosis after patient evaluation: the suspected symptoms are more often due to other, unrelated causes, such as cellulitis, Baker's cyst, musculoskeletal injury, or lymphedema. Other differential diagnoses include hematoma, tumors, venous or arterial aneurysms, and connective tissue disorders.

Anticoagulation, which prevents further coagulation but does not act directly on existing clots, is the standard treatment for deep vein thrombosis. Other, potentially adjunct, therapies/treatments may include compression stockings, selective movement and/or stretching, inferior vena cava filters, thrombolysis, and thrombectomy.

In any case, treatment of various venous maladies, including those described above, can be improved with stents. Improvements in stents for venous use are therefore desired.

BRIEF SUMMARY OF THE INVENTION

Accordingly, the present invention is directed to an intravascular stent that obviates one or more of the problems due to limitations and disadvantages of the related art. Disclosed herein are self-expending stents that include circumferential rings of alternating interconnected struts connected by flexible connectors. For example, the inventors have designed the struts of the rings and flexible connectors with structure, including areas of expanded or reduced width or thickness, to account for venous applications. As another example, the inventors have recognized that venous applications benefit from configurations that improve flexibility (due to the greater elasticity of venous applications) while maintaining enough stiffness to resist pressure on the venous structure in selected areas (such as for the May-Thurner syndrome). To that end, inventions disclosed herein include particular structural characteristics—often expressed as ratios between different measurements—that the inventors have determined are particularly advantageous for (although not limited to) venous applications.

In one embodiment, a stent defines a lumen having a longitudinal axis. The stent includes a plurality of cylindrical rings and flexible connectors. The cylindrical rings are spaced along the longitudinal axis. Each of the cylindrical rings includes a plurality of struts interconnected to form alternating apexes and troughs. Each of the struts has a main strut width and an apex strut width. The flexible connectors extend between adjacent pairs of the cylindrical rings. Each of the flexible connectors includes a main connector width, an apex, an apex connector width and a pair of ends. Each of the pair of ends is connected to one of the struts of the cylindrical rings between the apexes of the strut. The stent also includes a strut ratio of the apex strut width to the main strut width. A connector ratio is included of the apex connector width to the main connector width. In one embodiment, the strut ratio is 50% to 95% and the connector ratio is 50% to 95%.

In another embodiment, each of the flexible connectors includes a connection location ratio of 60% to 90% of a length of the strut to which the end is connected. In other embodiments, the strut ratio may be 60% and up to and including about 80%. The connection location ratio may be about 83%.

In other embodiments, the flexible connectors may have a length of 1.3 mm to 2.25 mm, including a length of about 1.7 mm. The length of each of the flexible connectors may be between 77% and 130% a length of the strut to which the end is connected, such as a length the same (100%) of the strut to which it is connected.

In other embodiments, the flexible connectors have different shapes, such as a V-shape and an S-shape.

In another embodiment, the ends of the flexible connectors may, connect to circumferentially offset struts. Also, the may be circumferentially offset by at least one intervening apex.

Another embodiment includes a method of delivering the stent. The method includes crimping a stent onto a catheter including radially compressing and lengthening a plurality of rings connected by flexible connectors. Also, the method includes expanding the stent by expanding the rings to an enlarged diameter resulting in a shorter axial length of the rings. Also, avoiding foreshortening of the stent upon expansion by lengthening the connectors via a connector ratio of an apex connector width to a main connector width of 50% to 95%.

Avoiding foreshortening can also include reducing shortening of the rings via a strut ratio of an apex strut width to a main strut width of 50% to 95%. Further, the method can include delivering the stent into a vein and deploying the stent out of the catheter with near zero foreshortening. Avoiding foreshortening can further include use of a connection location ratio of 60% to 90% of a length of a strut to which an end of the flexible connector is connected.

Other embodiments of the invention include any of the ranges (or points within the ranges) alone and in combination with each other disclosed herein in FIGS. 13 and 14. For example, the ratio ranges (expressed in percentages rather than fractions) are from about 65% to 91% for connector attachment location ratio, 70% to 108% for connector length ratio, 62% to 94% for strut-apex width ratio and 60% to 91% for connector-apex width ratio. Tighter ranges include 77% to 88% for connector attachment location ratio, 92% to 99% for connector length ratio, 76% to 86% to for strut-apex width ratio and 72?/o to 80% to for connector-apex width ratio. Notably also, those ranges where they fall below the baseline stent line (about 2% foreshortening) have particularly reduced foreshortening.

For another example, the larger range ratios include a connector length ratio from 80% to 112%, connector location attachment ratio from 66% to 90%, strut-apex width ratio from 67% to 95% and connector-apex width ratio from 66% to 92%. The tighter range ratios include a connector length ratio from 92% to 101%, a connector location attachment ratio from 76% to 84%, strut-apex width ratio from 80% to 88% and connector-apex width ratio from 75% to 82%.

In other embodiments, the ranges disclosed above are further limited to be below the baseline stent 2% foreshortening line on FIGS. 13 and 14.

Further embodiments, features, and advantages of the intravascular stent, as well as the structure and operation of the various embodiments of the intravascular stent, are described in detail below with reference to the accompanying drawings.

It is to be understood that both the foregoing general description and the following detailed description are exemplary and explanatory only, and are not restrictive of the invention as claimed.

BRIEF DESCRIPTION OF THE DRAWINGS

The accompanying figures, which are incorporated herein and form part of the specification, illustrate an intravascular stent. Together with the description, the figures further serve to explain the principles of the intravascular stent described herein and thereby enable a person skilled in the pertinent art to make and use the intravascular stent.

DETAILED DESCRIPTION

The inventors have observed certain problems in the prior art associated with foreshortening of stents, and in particular foreshortening of stents used for venous applications. Open-cell designed stents include rings connected together with bridge or connector struts. Closed cell designs, such as braided stents, include more of a mesh along the length. In either open or closed cell designs, there includes an inherent amount of foreshortening that occurs. Open cell designs can foreshorten 15-25%, depending on how the connectors are designed, and closed cell can foreshorten as much as 50%.

Foreshortening causes difficulty in accurately placing the stent in the patient's lumen, since the end which exits the delivery system first will either move the lumen or move in the lumen, toward the constrained end during the deployment. Additionally, this movement can cause trauma to the already compromised/fragile lumen being treated.

Accurate placement is ideal in all medical interventions, but it is vital in areas where the end that is first deployed is critical. Such areas include at vessel bifurcations and branch vessels, so that the implant does not enter or interfere with the portion of the vessel that does not require treatment. Such a bifurcation is present at the inferior vena cava where it branches into right and left iliac veins, as described in more detail below.

Figure 1:
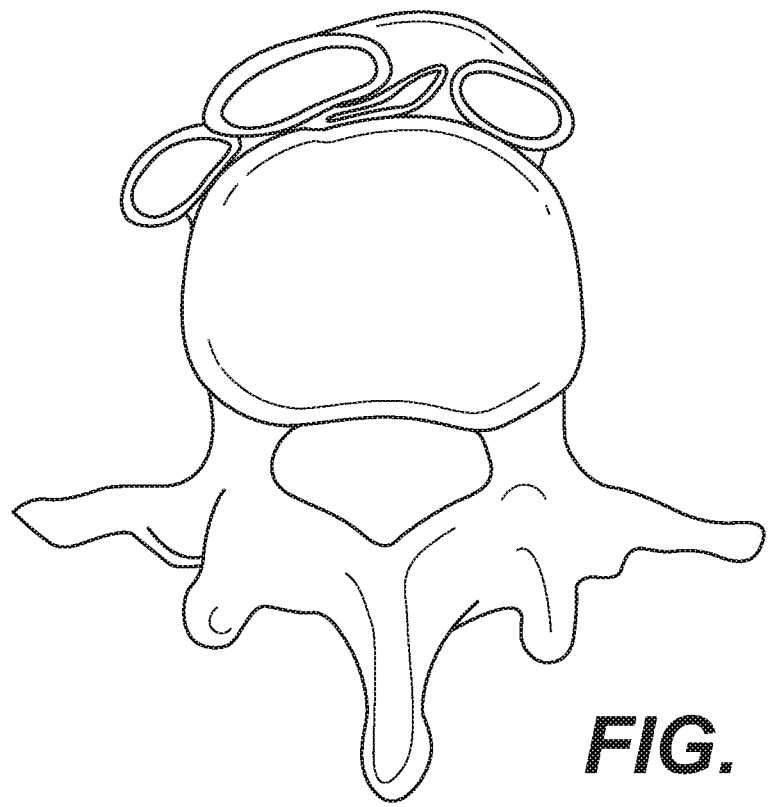
FIG. 1 shows an inferior-posterior view of the L5 lumbar and the bifurcations of the abdominal aorta and inferior vena cava.

May-Thurner syndrome, or iliac vein compression syndrome, occurs in the peripheral venous system when the iliac artery compresses the iliac vein against the spine as shown in FIG. 1. FIG. 1 illustrates a vertebra, the right and left common iliac arteries near the bifurcation of the abdominal aorta, and the tight and left common iliac arteries near the bifurcation of the inferior vena cava. The bifurcations generally occur near the L5 lumbar vertebra. Thus, it can be seen that FIG. 1 shows an inferior-posterior view of the L5 lumbar and the bifurcations of the abdominal aorta and inferior vena cava.

As shown, the strong right common iliac artery has compressed the iliac vein causing it to become narrowed. This is one possible, if not a classic, manifestation of May-Thurner syndrome. Over time, such narrowing may cause vascular scarring which can result in intraluminal changes that could precipitate iliofemoral venous outflow obstruction and/or deep vein thrombosis. As discussed above, venous insufficiency (i.e., a condition in which the flow of blood through the veins is impaired) can ultimately, lead to various deleterious pathologies including, but not limited to, pain, swelling, edema, skin changes, and ulcerations. Venous insufficiency is typically brought on by venous hypertension that develops as a result of persistent venous obstruction and incompetent (or subcompetent) venous valves. Current treatments for venous outflow obstruction include anticoagulation, thrombolysis, balloon angioplasty and stenting.

Figure 2:
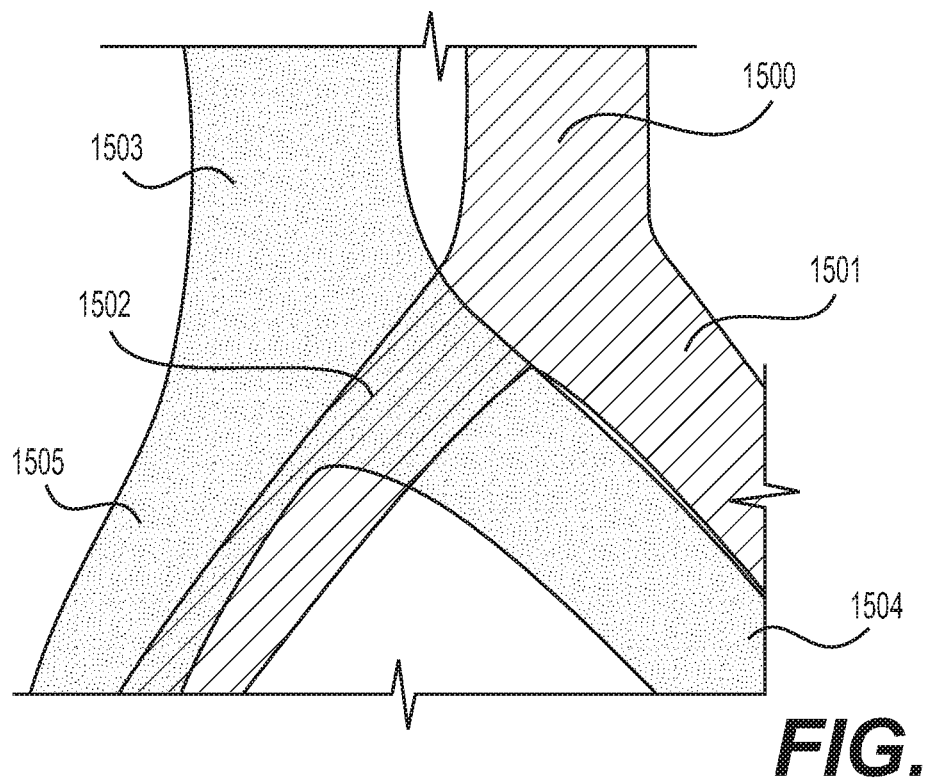
FIG. 2 shows a schematic of the standard overlap of the right common iliac artery over the left common iliac vein.

FIG. 2 illustrates the standard overlap of the right common iliac artery over the left common iliac vein. The arteries shown include the abdominal aorta 1500 branching into the left common iliac artery 1501 and the right common iliac artery 1502. The veins shown include the inferior vena cava 1503 branching into the left common iliac vein 1504 and right common iliac vein 1505. It will be understood that the rough diagram illustrated in FIG. 2 represents the view looking down on a patient laying face-up (i.e., an anterior-poster view of the patient at the location of the bifurcation of the abdominal aorta 1500 and the inferior vena cava 1503). The overlap of the right common iliac artery 1502, which is relatively strong and muscular, over the left common iliac vein 1504 can cause May-Thurner syndrome by pressing down on the vein 1504, crushing it against the spine, restricting flow, and, eventually, causing thrombosis and potentially partially or completely, clotting off of the left common iliac vein 1054 and everything upstream of it (i.e., the venous system in the left leg, among others).

Figure 3:
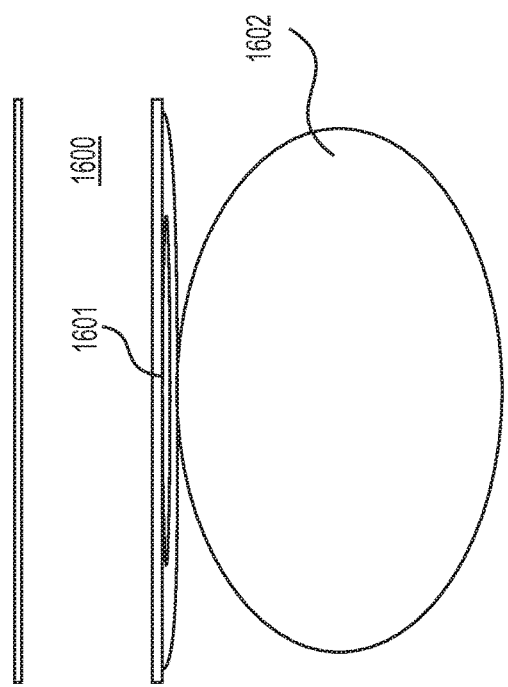
FIG. 3 shows a cross-sectional schematic of the arterio-venous system shown in FIG. 2 taken along the gray dotted line.

FIG. 3 illustrates a cross-section of the arterio-venous system shown in FIG. 2 taken along the gray dotted line. Shown in schematic are the right common iliac artery 1600, the left common iliac vein 1601, and a vertebra 1602 of the spine (possibly the L5 lumbar vertebra of the lumbar spine). As can be seen, the right common iliac artery 1600 is substantially cylindrical, due to its strong, muscular construction (among other potential factors). That strong, muscular artery has pressed down on the left common iliac vein 1601, until it has almost completely lost patency, i.e., it is nearly completely pinched off. It will be understood that May-Thurner syndrome may indeed involve such severe pinching/crushing of the underlying left common iliac vein 1601 against the vertebra 1602 of the lumbar spine. However, it will also be understood that May-Thurner syndrome may involve much less pinching/crushing of the underlying left common iliac vein 1601 against the vertebra 1602. Indeed, embodiments disclosed herein are appropriate for the treatment of various degrees of May-Thurner syndrome, including full crushing/pinching of the left common iliac vein 1602 by the right common iliac artery 1600. Other embodiments disclosed herein are appropriate for the treatment of various degrees of May-Thurner syndrome, including, but not limited to a crush/pinch of the underlying left common iliac vein 1601 of between about 10-95%, about 15-90%, about 20-85%, about 25-80%, about 30-75%, about 35-70%, about 40-65%, about 45-60%, and about 50-55%, or any other crush/pinch that could merit treatment using one or more of the devices disclosed herein.

Generally, disclosed herein are self-expending stents that include circumferential rings of alternating interconnected struts connected by flexible connectors. For example, the inventors have designed the struts of the rings and flexible connectors with structure, including areas of expanded or reduced width or thickness, to account for venous applications. As another example, the inventors have recognized that venous applications benefit from configurations that improve flexibility (due to the greater elasticity of venous applications) while maintaining enough stiffness to resist pressure on the venous structure in selected areas (such as for the May-Thurner syndrome). To that end, explored herein are particular structural characteristics—often expressed as ratios between different measurements—that the inventors have determined are particularly advantageous for (although not limited to) venous applications.

In one embodiment shown in FIGS. 4-7, a stent 10 of the present invention includes a plurality of rings 12 connected by a plurality of connectors 14, The rings 12 are arranged in a spaced relationship along a long axis 16 of the stent 10. The connectors 14 extend between adjacent pairs of the rings 12. Each of the rings and connectors are comprised of a plurality of interconnecting struts. The dimensions and orientation of these struts are designed to provide flexibility and radial stiffness in combination with substantially reduced or, for practical purposes in venous applications, "zero" foreshortening that is in particular advantageous for use in venous applications.

Notably the stents herein are not necessarily limited to venous applications unless specifically required by the claims. The disclosed stents could be employed in arterial and biliary applications, for example. But, are particularly suited for the demands of relatively soft structures defining lumens that are subject to much greater bending, twisting, stretching and other contortions and loads than are general atrial lumens.

Figure 6:
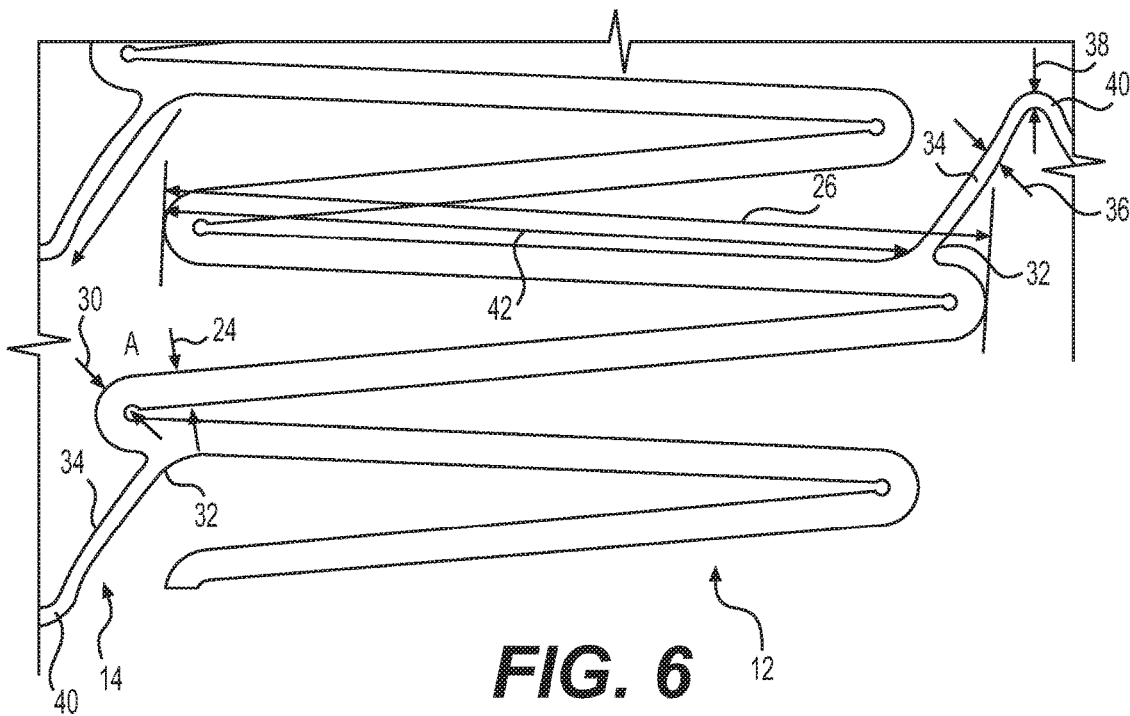
FIG. 6 shows a further enlarged view of FIG. 5.

Each of the rings 12 is comprised of a plurality of ring struts 18 interconnected to form alternating peaks or apexes 20 and troughs 22. As shown in FIG. 6, each of the ring struts 18 is generally straight and has a main strut width 24 and a strut length 26. The main strut width 24 is the width of the strut in the circumferential direction but adjusted to be at about a right angle to the edge of the strut. In other words, the main strut width 24 is an edge to edge measurement corresponding to the outermost circumferential surface of the struts of the rings 12.

It should be noted that terms such as perpendicular, thickness and other dimensional and geometric terms should not be regarded as strict or perfect in their application. Instead, geometric and other dimensional reference terms should be interpreted based on their correspondence to accepted manufacturing tolerances and functional needs of the stent 10 on which they are employed. For example, the term "perpendicular" should be appreciated as affording a reasonable amount of angular variation due to manufacturing imperfections or the actual intentional curves cut or formed in the stent design 10. Also, any thickness, width or other dimension should be assessed based on tolerances and functional needs of the design rather than idealized measurements.

Figure 4:
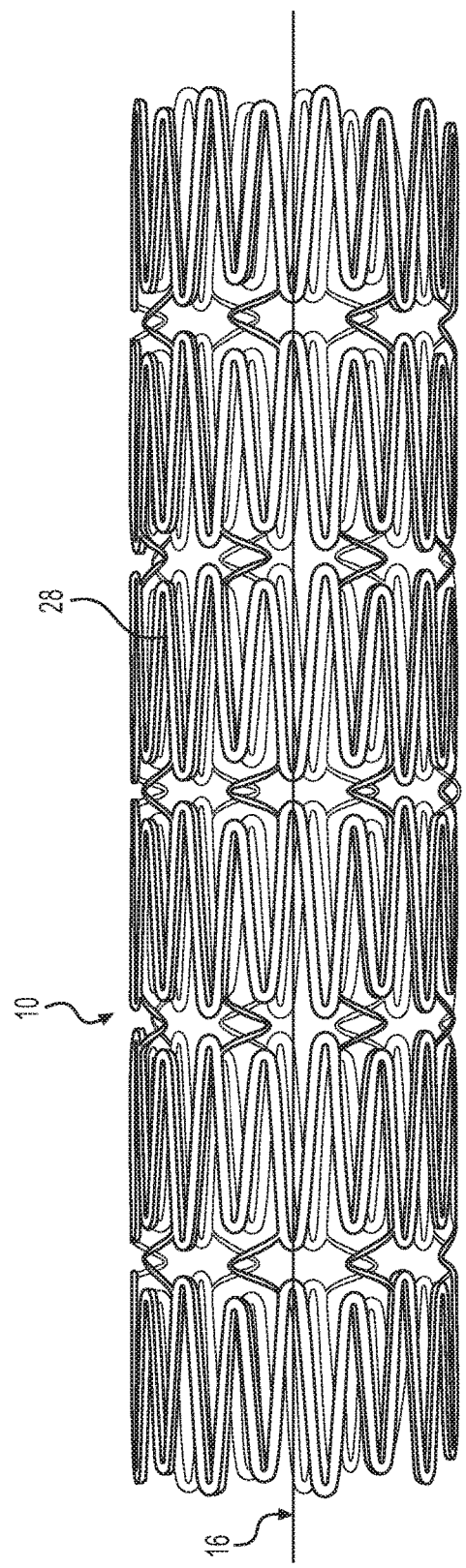
FIG. 4 shows a perspective view of a stent of one embodiment with circumferential rings of struts connected by flexible connectors.

The thickness 28 of the strut, on the other hand, is its depth in the radial direction which is generally perpendicular to the strut width measurement, as shown in FIG. 4. The strut thickness 28 normally corresponds to the wall thickness (outside diameter minus inside diameter) of the tube from which the stent 10 is laser cut after etching, grinding and other processing. But, embodiments of the stents disclosed herein are not necessarily limited to being laser-cut from a cylindrical tube with a predetermined wall thickness. They could also be formed or cut from flat sheets that are welded together at long edges to form a tube-like structure.

In the embodiment shown in FIG. 6, the ring struts 18 have a relatively consistent or constant width 24 in between the apexes 20 and troughs 22. Similarly, the ring strut thickness 28 is relatively constant along its length between the apexes 20 and troughs 22. The width and thickness of the ring struts could, however, vary along the length of the struts. In which case a "main" strut width would be at least the minimum of the widths between the apexes and troughs assuming uniform material strength along the strut. Generally, then, the main strut width is the width at which the strut has its greatest functional flexibility. Usually, for homogenous material properties, the main strut width will be the minimum strut width. However, the main strut width may be located at a wider portion if the material were configured to be generally less stiff than thicker regions even at greater widths.

In some embodiments, the ring struts 18 have some change in width as the approach the apexes 20 or the connectors 14. For example, struts in FIG. 6 taper somewhat as they enter the troughs 22. Tapering can, for example, improve clearance for compression of the ring struts 18 against each other in a crimping operation. Conversely, in some (or the same) embodiments, the ring strut widths increase as they approach the connectors 14. For example, as shown in FIG. 6, the ring strut enlarges where the connector 14 merges with the strut and on the side of the ring strut opposite the merging connector, the strut enlarges somewhat. Thus, the ring struts 18 enlarge a bit on both sides proximate the merging end of a connector 14.

Figure 5:
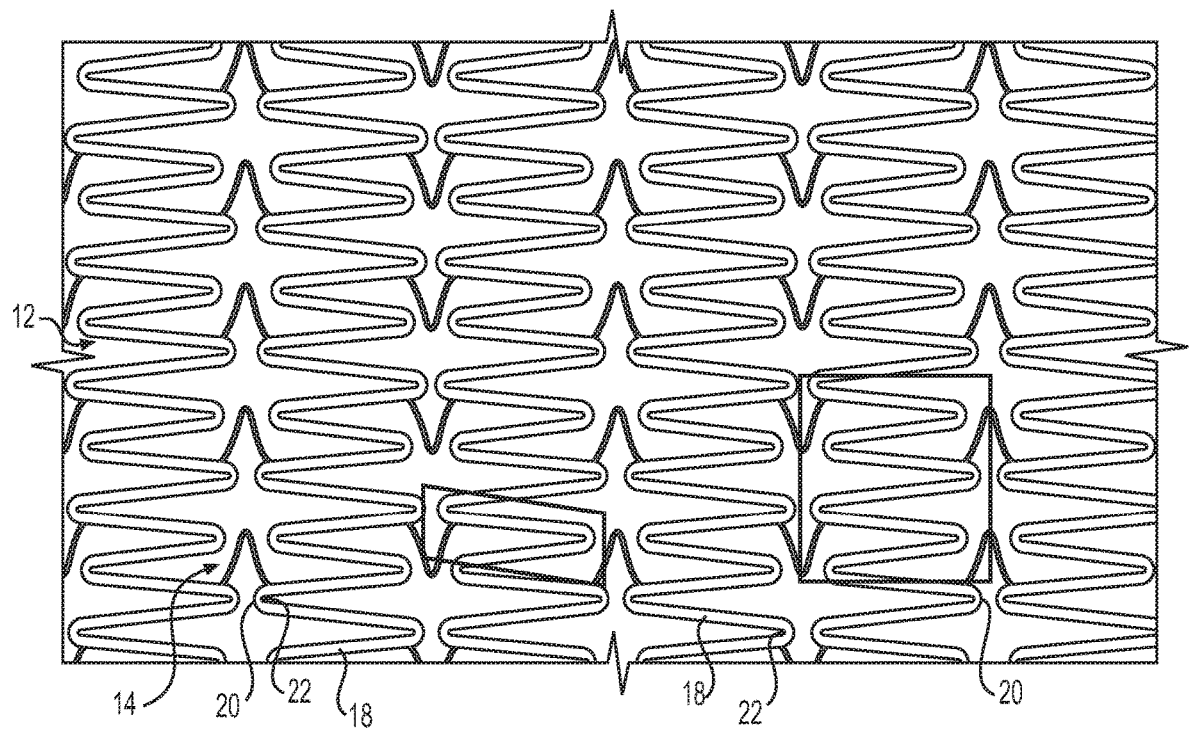
FIG. 5 shows an enlarged view of the stent of FIG. 4 with the stent opened up and laid flat.

As shown in FIGS. 5 and 6, the rings 12 are formed with alternating apexes 20 and troughs 22 because the struts are arranged having connected ends in a "zigzag" pattern. Restated, each of the apexes is paired with a corresponding trough on the opposite longitudinal side of the two adjacent, intersecting struts 18 and apexes and troughs alternate in the circumferential direction. Also notable is that each pair of apexes 20 on adjacent rings (connected by the connectors 14) extend in the longitudinal direction further than the next, circumferentially adjacent pair of apexes that are not connected by connectors 14. An advantage of this arrangement is that the two further peaks provide clearance for the circumferentially pointing connectors 14, especially in a compressed configuration. Also, the longitudinally closer apexes 20 provide additional length for supporting the connectors 14. In any case, the amplitude of the apexes 20 can be varied in embodiments to address different functional or geometric requirements. In the illustrated embodiment of FIGS. 5 and 6, the troughs 22, because of the extended peaks 20 at the connectors, are deeper on the opposite side of those higher amplitude peaks and shallower (in the longitudinal direction) opposite the non-connected peaks of the rings 12.

The apexes 20 are formed of the intersection of each of the ring struts 18 and, in some embodiments, have a curved structure where the struts change direction to extend back on themselves in the longitudinal direction, as shown in FIG. 6. The struts 18 (which are part of the struts formed into connections) at the apexes 20 of the ring struts 18 have an apex width 30 that is the smallest width of the apex in the span between the ends of the relatively straighter portions of the struts 18. Generally, as shown in the illustrated embodiments, the apex strut width 30 of the ring struts 18 is relatively constant. But, the apex strut width 30 of the ring struts 18 can vary, depending upon the desired variation in flexibility or material stiffness, for example, along its length.

As shown in FIGS. 4-6, the plurality of connectors 14 has a generally. V-shape and extends between adjacent, facing apexes 20 of the adjacent rings 12. For the embodiment of FIGS. 4-6, the connectors 14 connect alternate peaks, but the frequency of such connections can be varied depending on desired flexibility of the stent 10 with recognition that too few connectors 14 could result in fish scaling or other bending anomalies that would interfere with effective function. In any case, other examples of connector shape and frequency and connection location are described hereinbelow to illustrate that such variations are possible and still within the scope of the present invention.

Each of the connectors 14 itself is comprised of a plurality (e.g., a pair) of connector struts 34, an end 32 of each connector strut 34 connects to a respective ring strut 18. Each connector strut 34 in a plurality extends from its end that is connected to the respective ring strut 18 in a respective ring 12 to a shared apex 40 so as to form the V-shape. The connector struts 34—similar to the ring struts 18 of the exemplary embodiment—have a relatively constant width except where they connect to the rings 12. As with the ring struts 18 described above, the width of the connector struts 34 enlarge somewhat as they merge into connections with the rings 12. The connector struts 34, advantageously accounting for some of the increased stresses in the connection regions.

As shown in FIG. 6, for example, each of the connectors 14 also includes a main connector width 36 (between arrows) and an apex connector width 38 (between arrows). The main connector width 36 is the width of the connector strut 34, usually the minimum width or width expressing the area of highest flexibility, of the strut between the rings 12 and the connector apex 40. The apex connector width 38, as also labelled for example on FIG. 6, is the width of the connector apex 40 somewhere along its bend, such as in the middle of the bend. In any case, the apex connector width 38 can be a structural expression of an area of high flexibility on the connector apex 40.

Notably, in one embodiment, the connectors 14 do not connect directly to or at the apexes 20 of the rings 12. Instead, they are offset somewhat along the length of the ring struts 18 to which they are connected. Another meaningful metric for the structure of the stent 10 is the location of the connection of the ends 32 of the connectors 14 along the total strut length 26, as shown in FIG. 6. Each of the ends 32 of the connectors 14, for example, connects some connector distance 42 from the opposite apex 20 (the apex on the other end of the ring strut 18) that is less than the total distance between apexes (as measured from their outside radial surface) representative of the total strut length 26. The metric, therefore, can be in the form of the ratio of the distance of the connector to the opposite end, as compared to the total strut length 26. Thus, a connection at the apex 20 would be 100% and a connection in the middle of the strut would be 50%.

The connectors 14 may also be expressed or described as a ratio of their overall length (or in the case of connectors with an apex, the length between an end of the connector and the apex—such as ½ the total length for V-shaped strut of FIG. 6) compared to a baseline such as 1.7 mm in the illustrated embodiments. A different baseline could be used for different embodiments. The baseline for the ratio, for example, may also be a proportion of 30% to 50% the length of the ring struts 18. (In the illustrated embodiment, for example, the ring strut length can be about 3.4 mm yielding a baseline, using the 50% proportion, of 1.7 mm.)

In any case, the ratio of the connector length to the baseline can be, in embodiments, about 30% shorter (70% of the baseline) or longer (130% of the baseline). A longer connector 15 that is 2.2.5 mm is about 130% of the baseline 1.7 mm and 1.3 mm is only about 77% of the baseline 1.7 mm length. Generally, longer connectors are more flexible and thereby can provide more mediation of shortening of the rings 12 on expansion. But their length also can reduce the radial stiffness of the stent 10, resulting in an overall undesirable tradeoff (Strut length measurements can also vary somewhat and be measured from apex 20 to trough 22 or (as illustrated in FIG. 6) apex-to-apex.)

Figure 13:
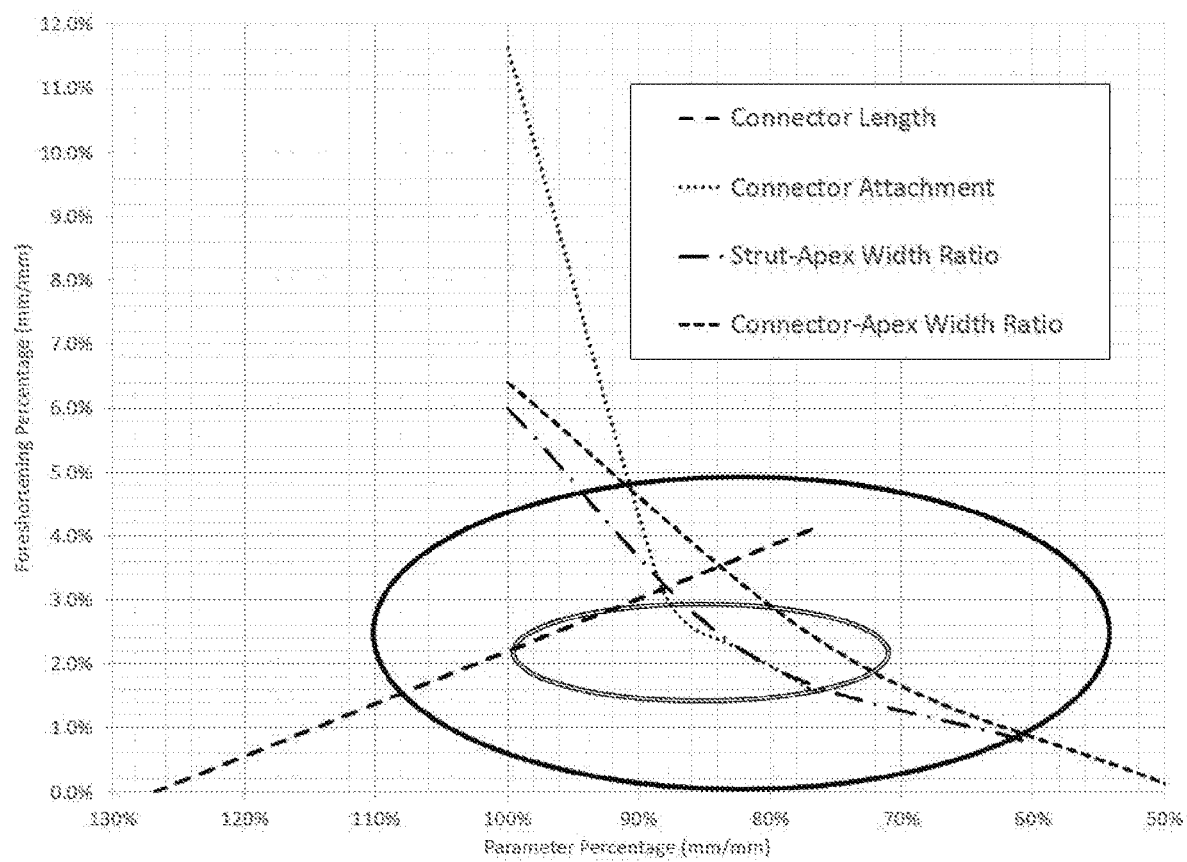
FIG. 13 shows the interplay between various non-dimensional ranges of the stent structures of various embodiments designed for venous and similar applications.

The inventors have redesigned the accepted prior art "typical" stent so as to improve (lessen) its foreshortening characteristics without concomitant equal loss in radial stiffness by assigning and modifying four or five parameters or metrics of the stent 10. Although other metrics are possible and can have some effects, the inventors have determined through design and testing these metrics can be arranged in particularly effective combinations as expressed by the graphical depiction in FIG. 13, FIG. 13 is an X-Y line graph with the vertical axis indicating the amount of foreshortening as a ratio of shortened amount divided by the original, unexpanded length of the stent 10. The horizontal axis expresses the non-dimensional (mm/mm) ratio of the particular parameters.

The parameters illustrated in FIG. 13 are connector length, connector attachment location ratio, strut to apex width ratio, and connector to connector-apex width ratio. Using the expression of connector length described above with respect to 1.7 mm, connector length in FIG. 13 is expressed as a ratio to the baseline embodiment stent connector length of 1.7 mm. For example, a 1.7 mm long connector is expressed as a "1" in the graph. Strut to apex width is the ratio of the apex strut width 30 divided by the main strut width 24. Connector width is the ratio of the apex connector width 38 to the main connector width 36. Further, connector location is expressed as a ratio of the connector distance 42 divided by the strut length 26. In other words, connector location is an expression of how far away from the apex 20 of the ring strut 18 the connector end 32 is attached. (Most typical struts have connectors connecting at the apexes 20 of the rings 12, hence the ratio "1" of a typical stent.)

The inventors have designed ranges that work particularly well for venous applications, such as those shown in FIG. 13 within the two ellipses. The outer ellipse represents a first set of collected ranges of connector location, apex width, connector width and connector length ratios that yield foreshortening ranges, flexibility and radial stiffness that have improved outcomes for venous applications. The inner ellipse represents a second, tighter set of ranges for further improved characteristics that have better outcomes for venous applications. A "baseline stent" threshold is also provided graphically such that a stent with parameters below the threshold line would—for treatment purposes—be considered a zero foreshortening stent (about 2% or less foreshortening). The lines associated with each of the ratios show the interplay between a particular changing parameter and the impact on foreshortening.

Referring again to FIG. 13, which is most applicable to stent geometries with rings and flexible connectors having at least one apex and connecting adjacent peaks of the rings, such as shown in FIGS. 4-11, the ratio ranges (expressed in percentages rather than fractions) are from about 65% to 91% for connector attachment location ratio, 70% to 108% for connector length ratio, 62% to 94% for strut-apex width ratio and 60% to 91% for connector-apex width ratio. Tighter ranges include 77% to 88% for connector attachment location ratio, 92% to 99% for connector length ratio, 76% to 86% to for strut-apex width ratio and 72% to 80% to for connector-apex width ratio. Notably also, those ranges where they fall below the baseline stent line have particularly reduced foreshortening.

In various other embodiments, ranges of the parameters include a strut ratio of the apex strut width to the main strut width of 50% to 95% along with a connector ratio of the apex connector width to the main connector width of 50% to 95%. The inventors determined these ranges reduce foreshortening of the stent along the longitudinal axis upon radial expansion. Also, the connection location ratio can be about 60% to 90% of a length of the strut to which the end is connected.

Particularly effective ratios were determined to be a strut ratio of 60% up to and including about 80%. The connector ratio can be about 75% and the connection location ratio about 83% for a preferred stent that balances flexibility, radial stiffness and constrained foreshortening. According to principles of some embodiments of the present invention, flexible connector lengths for venous applications may range from 1.3 mm to 2.25 mm with a good performance found at 1.7 mm. Also according to principles of some embodiments, the length of each of the flexible connectors may be within 77% to 130% of a length of the supporting strut, and good performance demonstrated at the same (100%) length.

Figure 10:
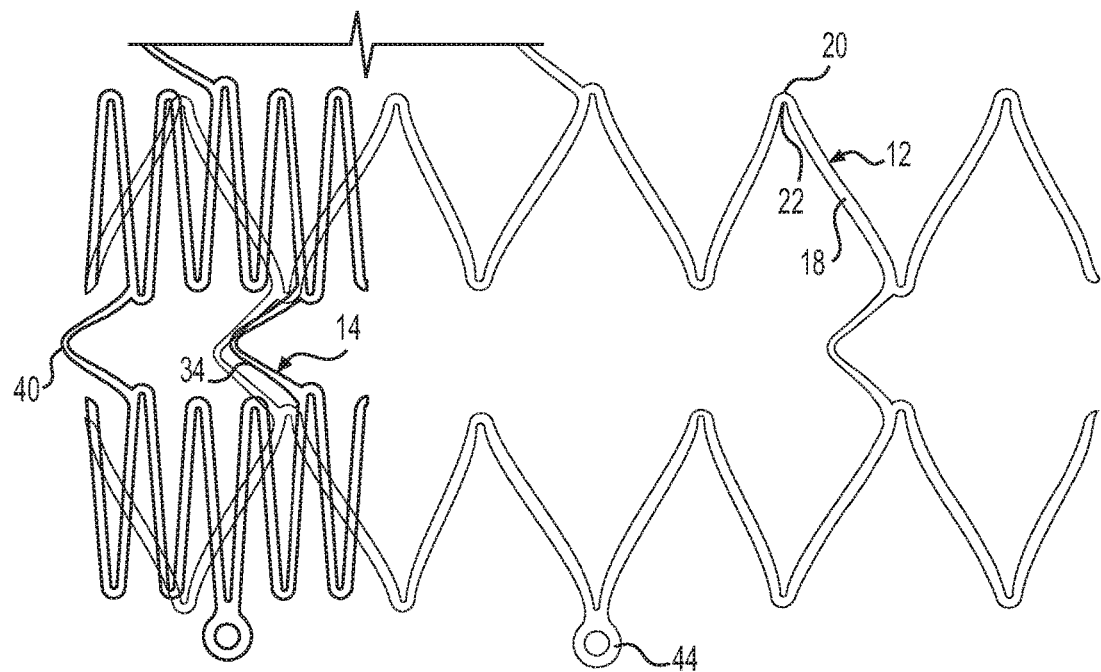
FIG. 10 shows a schematic of a stent of another embodiment at compressed and expanded configurations.

Embodiments of the stents disclosed herein include advantages such as a reduction of the typical 20% to 50% of foreshortening of conventional flexible stents, resulting in more accurate sizing and placement. Generally, the stent designs can include open celled designs that include connector or bridge members that expand in length as the rings shorten. Thus, foreshortening is reduced or avoided while the ring stiffness is preserved for vessel treatment. Design features that facilitate avoidance of shortening include attaching the connectors away from the apexes. As shown in FIG. 10, in this position, the strut-connector junction rotates as the ring expands. Also, the connectors are angled such that during ring expansion the angle of the connector decreases with the increasing angle of the strut. Decreasing connector angle causes the distance between rings 12 to increase offsetting foreshortening from increasing ring strut angle.

Figure 7:
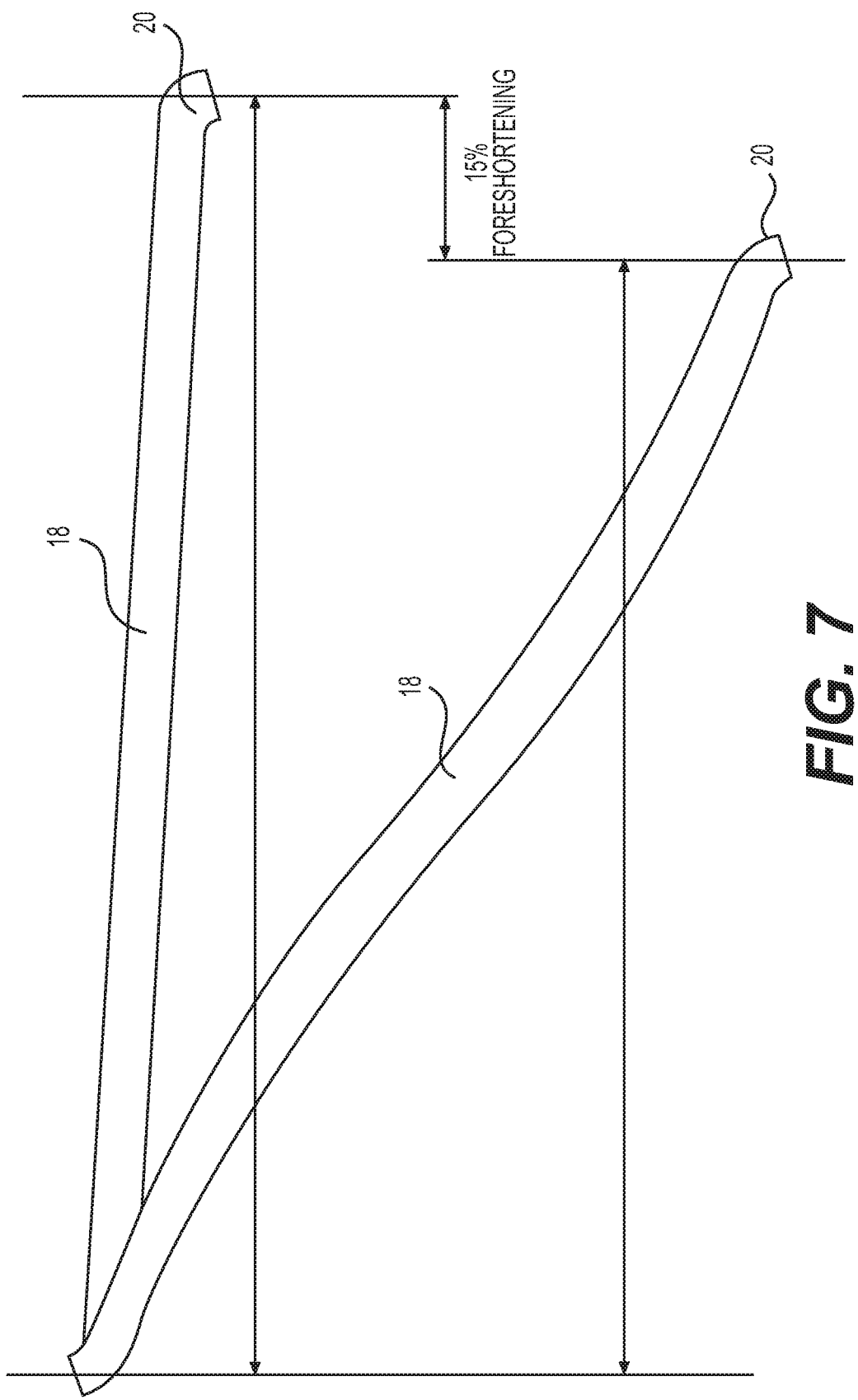
FIGS. 7-9 show mathematical models of stent rings and flexible connectors of different embodiments with various ranges of foreshortening.
Figure 8:
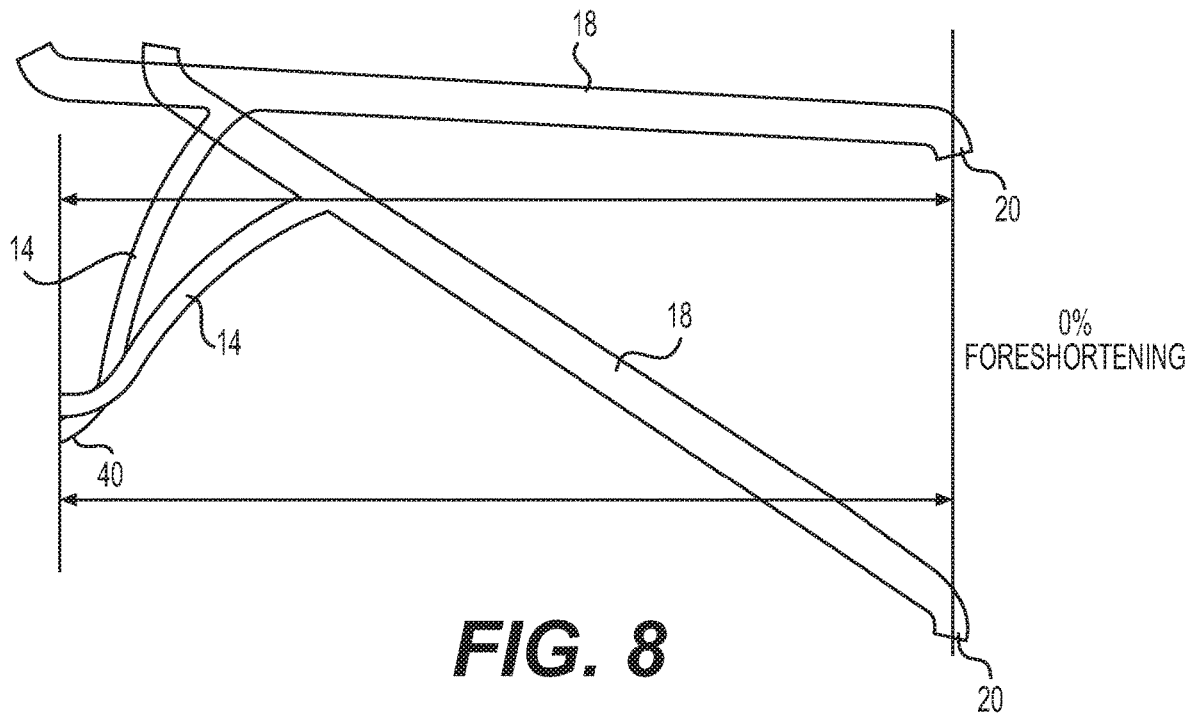
Figure 9:
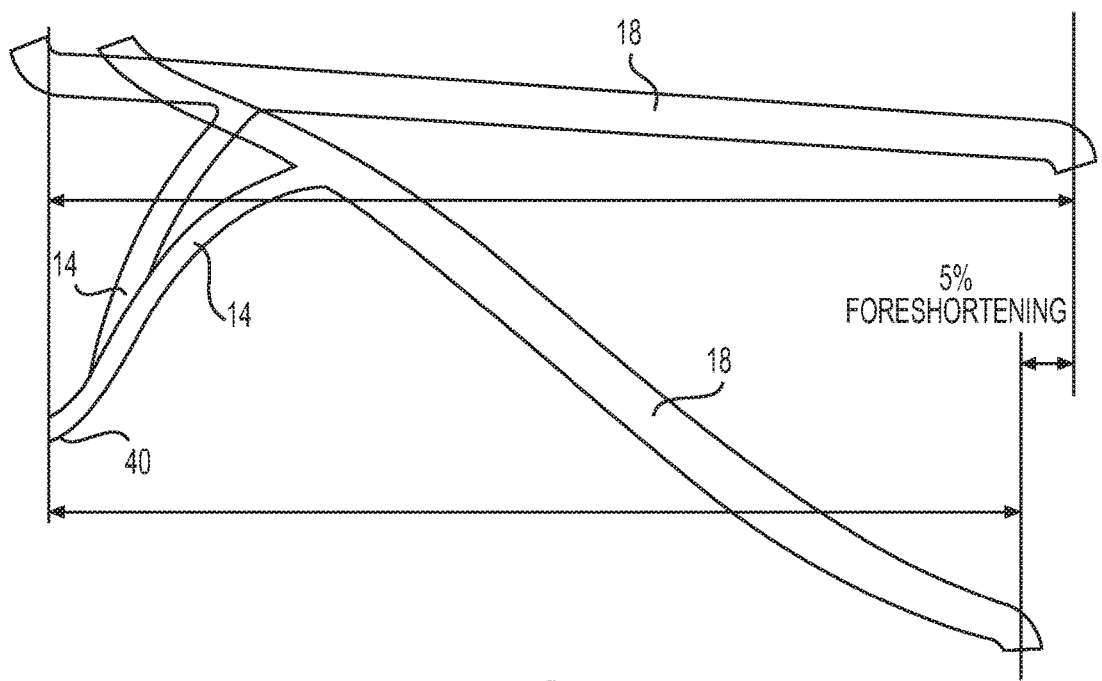

As shown in FIG. 7, a typical stent foreshortens 15% with the stresses in the ring struts being the heaviest at the apexes 20 undergoing the largest amount of bending. (The top of the figure shows the unstressed compacted strut and the bottom shows the ring strut expanded and shortened by 15%.) The rigidity and orientation of the ring struts 18 contribute to the shortening—their zigzag orientation resulting in an accordion effect. FIG. 8 shows a stent that would hinge at apexes 20 and all of the translation occurs via increasing length at the connector to offset shortening of the rings struts 18, with a net zero foreshortening. FIG. 9 shows a stent wherein the radial stiffness with strong and/or wide apexes 20 that is balanced with a length increase in the connectors—but with a resulting 5% foreshortening.

To deploy the implant, the implant may be radially compressed/crimped to a smaller diameter for loading onto/into a delivery catheter. The implant may be crimped over a balloon on the inner core of the delivery system which may be later inflated to expand the coiled implant to the desired diameter. The engagement fingers are pre-configured at specific locations to allow discrete incremental expansion of the stent. In some embodiments, the implant can be expanded in 0.5 mm increments. In some embodiments more than one implant may be joined together. For example, the ultimate length of the implant can be controlled by joining any desired number of individual adaptive diameter cells via flexible or rigid bridge members.

Implants such as those described above may be advantageously provide an adaptive diameter and/or flexibility to conform the dynamic movement of peripheral veins in leg/pelvis thereby facilitating treatment of both iliac vein compression syndrome and ilio-femoral venous outflow obstructions.

It may be desirable to have a stent that will conform to the existing path of a vein instead of a straightening out of the vessel by the stent. It may also be desirable to have a high radial stiffness of the stent to resist collapse of the stent under crushing load and to maximize the resultant diameter of the treated vessel at the location of the stent deployment. With most stent constructions there is a direct relationship between radial stiffness and axial stiffness.

Common commercially available balloon expandable stents experience a dramatic change in length as a balloon is used to expand the stent within the vessel. Common commercially available self-expanding stents experience a change in length less dramatic, but still substantial, which increases with increasing stent length. Change in length between the configuration within the delivery system and when deployed in the vessel causes difficulty in placing/landing the stent precisely at the target location. When the stent is deployed in its crimped configuration and expanded, the shortening in length causes the stent target deployment location to have to offset from the target dwell location. The magnitude of this effect is not controllable or easily anticipated as it is dependent on the luminal cross-section along the length of the target dwell location (which is frequently and unexpectedly influenced by residual stenosis, irregular shape due to external objects, and/or forces, etc.). For target lesions leading up to the junction of the left and right iliac into the IVC, this causes difficulty in placing the stent to dwell completely within the iliac along its total length up to the junction to the inferior vena cava without crossing into the inferior vena cava.

In some embodiments a venous stent with high radial force, no impactful foreshortening along multiple lengths, and high flexibility/vessel conformity is provided. Minimization of foreshortening allows the stent advantageously accurate and predictable deployment. And, high flexibility maximizes the fatigue life of the stent under bending. Of course, it will be understood that the stent may find applications in the arterial system as well.

Figure 11:
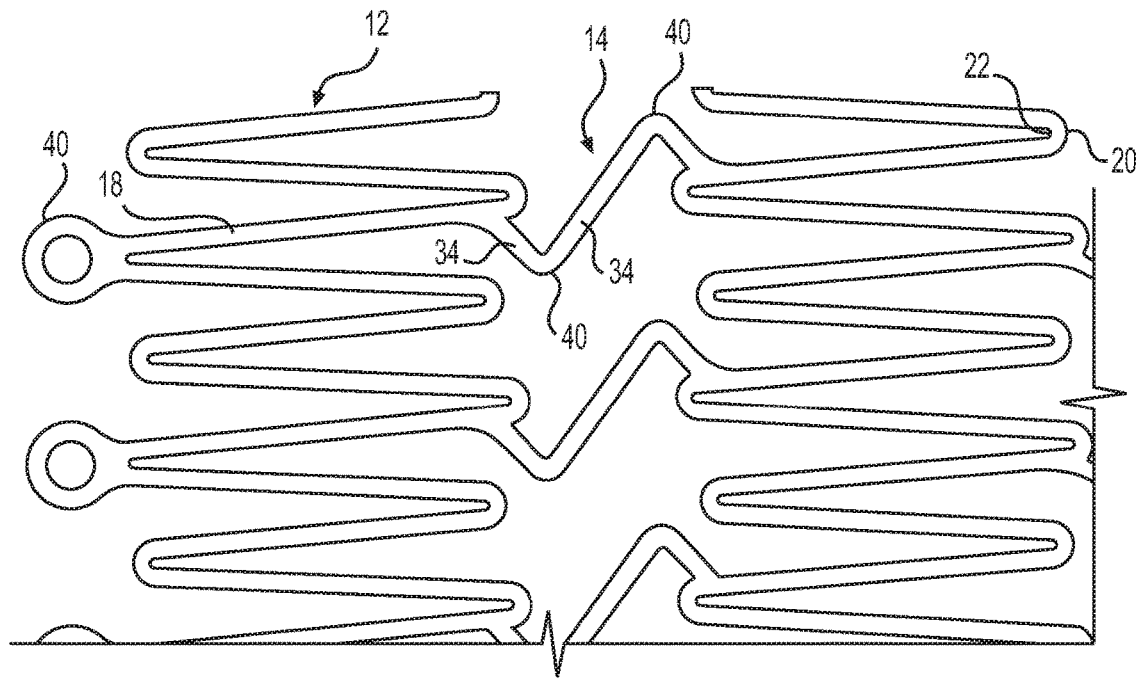
FIG. 11 shows a schematic of structure of a stent of another embodiment with an S-shaped flexible connector.
Figure 12:
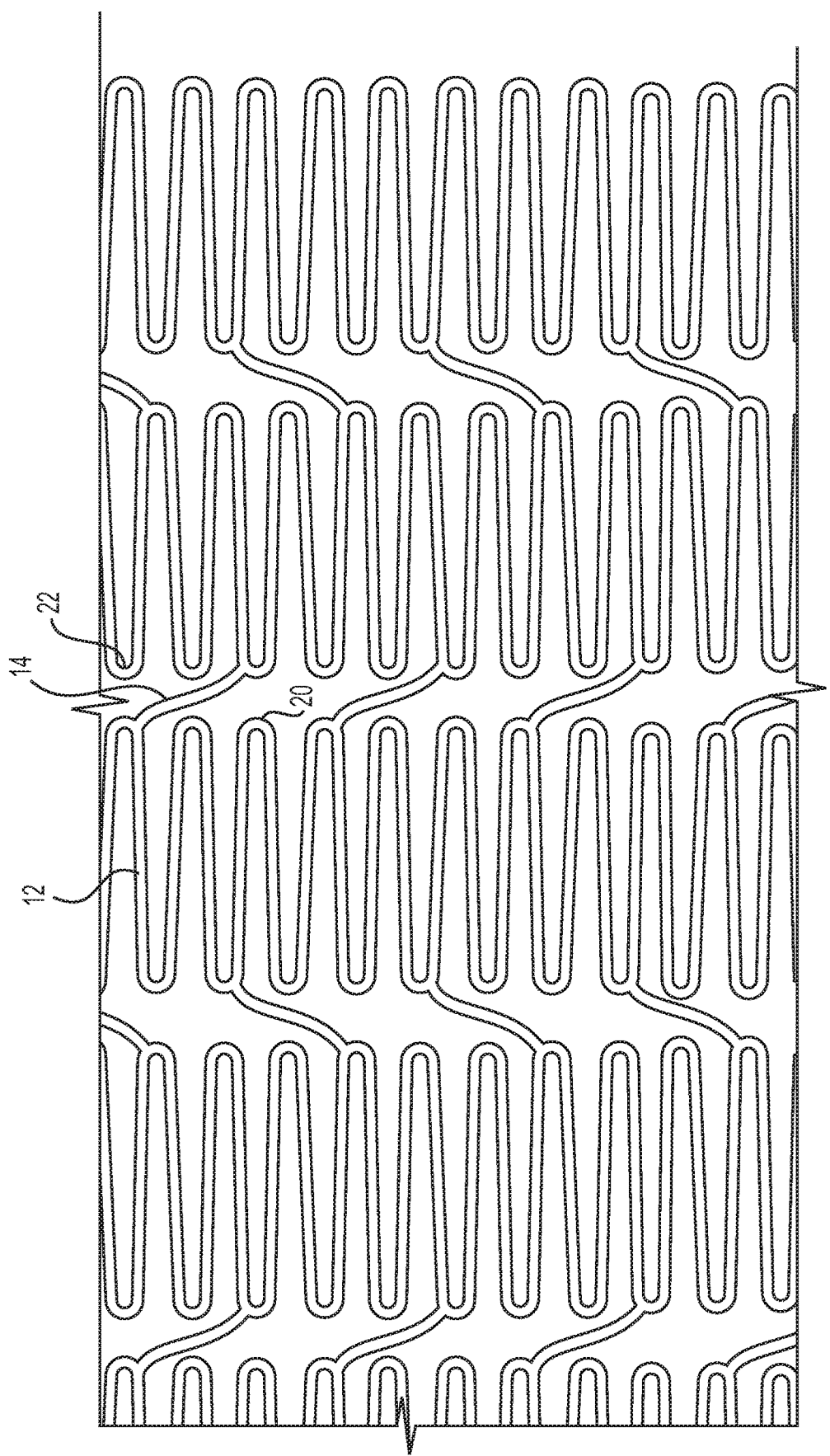
FIG. 12 shows a schematic of structure of yet another stent of another embodiment with flexible connectors extending between non-adjacent ring apexes.

FIGS. 11 and 12 illustrate various views of other embodiments of a stent 10 or stents configured to minimize foreshortening while retaining flexibility. FIG. 11 shows an S-shaped connector 14. For this S-shape, the two ends of the connectors attach to opposite sides of the opposing rings 12. Because of the additional apexes 40 in the connectors 14, there is additional flexibility afforded by the S-shape to counteract foreshortening of the rings. To that extent, the ratios then of apex to main connector width can be less than that of the single apex connectors. Additionally, the connectors 14 (of either configuration) could be designed such that in the crimped configuration, they are in contact with one another in a manner that pulls the rings together by the amount that the individual rings foreshorten during deployment.

FIG. 12 shows a stent 10 with a plurality of rings 12 with curved connectors 14 that have ends 32 connected to non-opposing apexes 20 of the rings. In particular, the illustrated embodiment connects to every third one of the apexes 20 and extends circumferentially in a slight s-curve. The connectors 14 connect apexes that are separated by an intervening apex, thus skipping the opposite apex and the apex adjacent to that opposite apex for a third apex. Thus, additional lengthening of the connectors 14 is facilitated by not only offsetting from the peak, but offsetting to a different apex. This feature could be combined with the other features disclosed herein to further mediate ring foreshortening.

Figure 14:
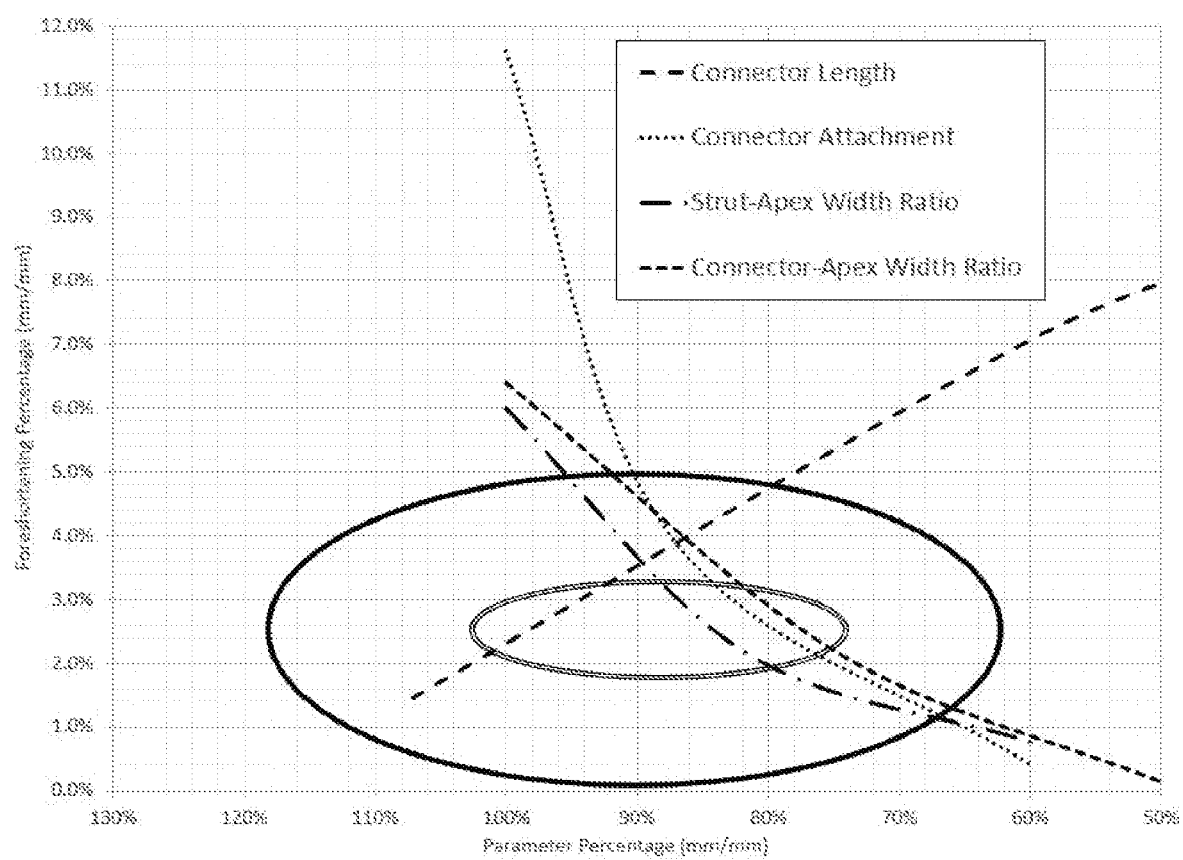
FIG. 14 shows the interplay between various non-dimensional ranges of the stent structures of various other embodiments, including the stent structure of FIG. 12, designed for venous and similar applications.

FIG. 14, like FIG. 13, shows ratios that work particularly well for stents with rings and connectors connecting non-adjacent peaks, such as is shown in FIG. 12. As applied to the embodiment of FIG. 12, the strut-apex width, connector-apex width, and connector attachment location ratios are calculated the same way as for FIG. 13. But, the connector length is calculated differently for FIG. 12. The connector length in this embodiment is the total length of the connector from apex to apex. For the embodiment of FIG. 6, the connector length is from the connection 32 to the apex 40 or half the total overall length of the connector. As above, the longer the connector length, the more foreshortening is reduced. Also, the further the connector is attached along the length of the strut, the more foreshortening is minimized. The larger range ratios include a connector length ratio from 80% to 112%, connector location attachment ratio from 66% to 90%, strut-apex width ratio from 67% to 95% and connector-apex width ratio from 66% to 92%. The tighter range ratios include a connector length ratio from 92% to 101%, a connector location attachment ratio from 76% to 84%, strut-apex width ratio from 80% to 88% and connector-apex width ratio from 75% to 82%. As with FIG. 13, the longer the connector length, the more that foreshortening is minimized. Also as with FIG. 13, the further the connector is attached along the length of the strut, the more foreshortening is minimized.

Embodiments disclosed herein can be used for both balloon expandable and self-expanding stent designs. The stent designs can be used for all stent interventions, including coronary, peripheral, carotid, neuro, biliary and, especially, venous applications. Additionally, this could be beneficial for stent grafts, percutaneous valves, etc.

Some embodiments disclosed herein, such as those shown in FIGS. 4-6, and 8-12, decouple the relationship between radial stiffness and axial stiffness through their configuration of individual one cell long rings fixed together at the joining of the cells of each ring through the linkage struts. This allows for maintenance of controlled spacing by the linkage strut between the joined rings along a pathway but gives them the freedom to orient with the axis of one ring being different than the axis of the adjacent rings. The individual rings, with a relatively low axial flexibility, orient themselves largely straight along their individual length with the bending happening substantially along the linkage struts which are characterized by a much higher axial flexibility. Therefore, radial force can be controlled by the width of the cell struts and kept independent of the axial flexibility that is controlled by the width of the linkage struts, Additionally, the axially rotated indexing position of each adjacent pair of linkage struts, creating a spiral orientation of linkage struts, ensures that the stent has substantially similar axial flexibility regardless of angular orientation around its axis.

With each cell connected at the attachment of the struts, there is no change in position of one cell to the adjacent cells when the stent is fully crimped and when it's fully unconstrained. Therefore, the only foreshortening of the stent would come from half of the leading cell and half of the trailing cell. Also, the foreshortening of the presented invention is the same regardless of stent overall length given equally configured cells (increasing length by adding more rings). When the presented invention is deployed into the iliac-inferior vena cava (as discussed above), the location of the stent within the delivery system will equal the location of the stent when deployed form the delivery system into the vessel. The positioning and deployment of the stent will be the same regardless of the stent length. Therefore, a marker located at the connection of the cells/attachment of the struts can give excellent visualization and indication of the position of the stent when in the delivery system and when deployed in the vessel.

Currently available implants are typically loaded and retained onto a delivery system in a crimped configuration and then navigated and deployed in the desired anatomical location where they expand to the implanted configuration. The final implanted configuration can be achieved through mechanical expansion/actuation (e.g., balloon-expandable) or self-expansion (e.g., Nitinol). Self-expanding implants are manufactured from super elastic or shape memory alloy materials. Accurate and precise deployment of a self-expanding implant can be challenging due to a number of inherent design attributes associated with self-expanding implants. The implant may jump/advance from the distal end of the delivery system during deployment due to the stored elastic energy of the material. Additionally, the implant may foreshorten during deployment due to the change in the implant diameter from the crimped configuration to the expanded configuration. Finally, physiological and anatomical configurations, such a placement at or near bifurcations of body lumens, can affect accurate placement of implants. Once the implant in placed within the body lumen there is potential for uneven expansion or lack of circumferential implant apposition to the body lumen which can result in movement, migration or in certain severe cases implant embolization.

In some embodiments, a self-expanding implant designed with sufficient radial force to resist constant compression of the body lumen while providing optimal fatigue resistance, accurate placement, and in-vivo anchoring to prevent is provided. Additionally, various methods for deployment and implantation for treating iliac vein compression syndrome and venous insufficiency disease are provided.

In some embodiments, the implant comprises a purposely designed venous implant intended to focally treat iliac vein compression (May-Thurner Syndrome). The implant may be relatively short in length (~40 mm) and may be manufactured from self-expending Nitinol with integrated anchor features to aid in accurate placement and to mitigate migration following implantation. The implant and delivery system are designed for precise deployment and placement at the bifurcation of the inferior vena cava into the right and left common iliac veins.

As another feature, the stents 10 disclosed herein can include anchor members or eyelets 44, as shown in FIGS. 10 and 11.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents.

What is claimed is:

1. A stent defining a lumen having a longitudinal axis, the stent comprising:
   a plurality of cylindrical rings spaced along the longitudinal axis, each of the cylindrical rings including a plurality of struts interconnected such that an apex and a trough is formed at the connection between each adjacent pair of struts, each of the struts having a straight portion extending between curved apex portions at opposite ends of the straight portion, and each of the struts having a strut length, a main strut width, and an apex strut width; and
   a plurality of flexible connectors extending between adjacent pairs of the cylindrical rings, each of the flexible connectors including a pair of connector struts each having a main connector width and each having opposite first and second ends, wherein the first ends of the pair of connector struts are connected together such that an apex connector having an apex connector width is formed, wherein the pair of connector struts are angled relative to one another when the stent is in a compressed configuration, and wherein the second ends of the pair of connector struts are respectively connected to the straight portion and spaced from the curved apex portion of one of the struts of adjacent cylindrical rings;
   wherein the apex strut width is less than the main strut width, and wherein the apex connector width is less than the main connector width so as to reduce foreshortening of the stent along the longitudinal axis upon radial expansion;
   wherein the plurality of struts of each of the cylindrical rings includes a plurality of first struts each having a first strut length and a plurality of second struts each having a second strut length that is less than the first strut length, and wherein each of the flexible connectors is connected to at least one of the first struts.

2. The stent of claim 1, wherein the plurality of struts of each of the cylindrical rings further includes a plurality of third struts each having a third strut length that is different from each of the first strut length and the second strut length.

3. The stent of claim 2, wherein the third strut length is greater than the first strut length.

4. The stent of claim 2, wherein the plurality of struts of each of the cylindrical rings includes one of the third struts that is connected to one of the first struts at a first apex and is connected to another of the first struts at a second apex.

5. The stent of claim 1, wherein the plurality of struts of each of the cylindrical rings includes one of the second struts that is connected to one of the first struts at a first apex and is connected to another of the first struts at a second apex.

6. The stent of claim 1, wherein each of the flexible connectors is connected to a pair of the first struts.

7. The stent of claim 1, wherein each of the flexible connectors is connected to circumferentially offset first struts.

8. The stent of claim 7, wherein the circumferentially offset first struts are offset by at least one intervening apex.

9. The stent of claim 1, wherein the main connector width is less than the apex strut width.

10. The stent of claim 1, wherein a strut ratio of the apex strut width to the main strut width is 50% to 95%.

11. The stent of claim 1, wherein a connector ratio of the apex connector width to the main connector width is 50% to 95%.

12. The stent of claim 1, wherein the second end of each pair of connector struts is connected to the straight portion of a first strut at a connection location of the first strut, and a connection location ratio between a length along the first strut to the connection location and the first strut length is 60% to 90%.

13. A stent defining a lumen having a longitudinal axis, the stent comprising:
   a plurality of cylindrical rings spaced along the longitudinal axis, each of the cylindrical rings including a plurality of struts interconnected such that an apex and a trough is formed at the connection between each adjacent pair of struts, each of the struts having a straight portion extending between curved apex portions at opposite ends of the straight portion, and each of the struts having a strut length, a main strut width, and an apex strut width; and a plurality of flexible connectors extending between adjacent pairs of the cylindrical rings, each of the flexible connectors including a connector strut having a main connector width, opposite first and second ends, and an apex having an apex connector width between the first and second ends, wherein each of the first and second ends of the connector strut is connected to the straight portion and spaced from the curved apex portion of one of the struts of the adjacent cylindrical rings;

wherein the apex strut width is less than the main strut width, and wherein the apex connector width is less than the main connector width so as to reduce foreshortening of the stent along the longitudinal axis upon radial expansion;

wherein the plurality of struts of each of the cylindrical rings includes a plurality of first struts each having a first strut length, a plurality of second struts each having a second strut length that is less than the first strut length, and a plurality of third struts each having a third strut length that is greater than the first strut length, and wherein each of the flexible connectors is connected to at least one of the first struts.

14. The stent of claim 13, wherein each of the flexible connectors is connected to a pair of the first struts.

15. The stent of claim 13, wherein each of the flexible connectors is connected to circumferentially offset first struts, and wherein the circumferentially offset first struts are offset by at least one intervening apex.

16. The stent of claim 13, wherein a strut ratio of the apex strut width to the main strut width is 50% to 95%, wherein a connector ratio of the apex connector width to the main connector width is 50% to 95%, and wherein the first end of the connector strut is connected to the straight portion of a first strut at a connection location of the first strut, and a connection location ratio between a length along the first strut to the connection location and the first strut length is 60% to 90%.

17. A stent defining a lumen having a longitudinal axis, the stent comprising:

a plurality of cylindrical rings spaced along the longitudinal axis, each of the cylindrical rings including a plurality of struts interconnected such that an apex and a trough is formed at the connection between each adjacent pair of struts, each of the struts having a straight portion extending between curved apex portions at opposite ends of the straight portion, and each of the struts having a strut length, a main strut width, and an apex strut width; and a plurality of flexible connectors extending between adjacent pairs of the cylindrical rings, each of the flexible connectors including a connector strut having a main connector width, opposite first and second ends, and an apex having an apex connector width between the first and second ends, wherein each of the first and second ends of the connector strut is connected to the straight portion and spaced from the curved apex portion of one of the struts of the adjacent cylindrical rings;

wherein the apex strut width is less than the main strut width, wherein the apex connector width is less than the main connector width, and wherein the main connector width is less than the apex strut width so as to reduce foreshortening of the stent along the longitudinal axis upon radial expansion;

wherein the plurality of struts of each of the cylindrical rings includes a plurality of first struts each having a first strut length and a plurality of second struts each having a second strut length that is less than the first strut length, and wherein each of the flexible connectors is connected to at least one of the first struts.

18. The stent of claim 17, wherein the plurality of struts of each of the cylindrical rings further includes a plurality of third struts each having a third strut length that is different from each of the first strut length and the second strut length.

19. The stent of claim 17, wherein each of the flexible connectors is connected to a pair of the first struts.

20. The stent of claim 17, wherein a strut ratio of the apex strut width to the main strut width is 50% to 95%, wherein a connector ratio of the apex connector width to the main connector width is 50% to 95%, and wherein the first end of the connector strut is connected to the straight portion of a first strut at a connection location of the first strut, and a connection location ratio between a length along the first strut to between the connection location and the first strut length is 60% to 90%.

* * * * *